(12) United States Patent
Tsujimori et al.

(10) Patent No.: US 8,796,447 B2
(45) Date of Patent: Aug. 5, 2014

(54) PROCESS FOR PRODUCING BENZO[B][1,4]DIAZEPINE-2,4-DIONE COMPOUND

(75) Inventors: Hisayuki Tsujimori, Osaka (JP); Shinichi Taira, Osaka (JP); Hirotaka Yukawa, Osaka (JP); Kaoru Abe, Osaka (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 13 days.

(21) Appl. No.: 13/391,468

(22) PCT Filed: Aug. 20, 2010

(86) PCT No.: PCT/JP2010/064040
§ 371 (c)(1),
(2), (4) Date: Feb. 21, 2012

(87) PCT Pub. No.: WO2011/021676
PCT Pub. Date: Feb. 24, 2011

(65) Prior Publication Data
US 2012/0149899 A1 Jun. 14, 2012

Related U.S. Application Data

(60) Provisional application No. 61/235,988, filed on Aug. 21, 2009.

(51) Int. Cl.
*C07D 243/12* (2006.01)
*C07D 243/14* (2006.01)

(52) U.S. Cl.
CPC ............ *C07D 243/12* (2013.01); *C07D 243/14* (2013.01)
USPC ...................................................... 540/518

(58) Field of Classification Search
USPC ........................................................ 540/518
See application file for complete search history.

(56) References Cited

U.S. PATENT DOCUMENTS

| | | | |
|---|---|---|---|
| 3,133,056 A | 5/1964 | Ash et al. | |
| 3,984,398 A | 10/1976 | Rossi | |
| 4,001,408 A | 1/1977 | Rossi | |
| 4,298,739 A | 11/1981 | Nishi et al. | |
| 4,435,404 A | 3/1984 | Nishi et al. | |
| 5,216,148 A | 6/1993 | Klaus et al. | |
| 7,321,001 B2 | 1/2008 | Fu et al. | |
| 2003/0158082 A1 | 8/2003 | Colclough et al. | |
| 2009/0264404 A1 | 10/2009 | Yamashita et al. | |

FOREIGN PATENT DOCUMENTS

| | | |
|---|---|---|
| EP | 0 450 066 A1 | 10/1991 |
| EP | 0 504 695 A1 | 9/1992 |
| EP | 0 569 592 A1 | 11/1993 |
| GB | 1 210 809 | 11/1970 |
| GB | 1 460 936 | 1/1977 |
| JP | 2-96133 A | 4/1990 |
| WO | 96 40654 A1 | 12/1996 |
| WO | WO 96/40655 A1 | 12/1996 |
| WO | 97/12869 | 4/1997 |
| WO | WO 01/10216 A1 | 2/2001 |
| WO | WO 01/77143 A2 | 10/2001 |
| WO | WO 2007/026959 A2 | 3/2007 |
| WO | WO 2009/104819 A1 | 8/2009 |

OTHER PUBLICATIONS

Supplementary European Search Report in EP Application 10810017.3 dated Jan. 8, 2013.
Office Action in U.S. Appl. No. 13/591,361 dated Dec. 27, 2012.
Office Action dated May 22, 2012 in U.S. Appl. No. 12/918,226.
Alan S. Go, et al., "Prevalence of Diagnosed Atrial Fibrillation in Adults: National Implications for Rhythm Management and Stroke Prevention: the AnTicoagulation and Risk Factors in Atrial Fibrillation (ATRIA) Study", The Journal of American Medical Association, May 2001, pp. 2370-2375, vol. 285, No. 18.

(Continued)

*Primary Examiner* — Bruck Kifle
(74) *Attorney, Agent, or Firm* — Sughrue Mion, PLLC

(57) ABSTRACT

A process for producing a compound represented by formula (1),

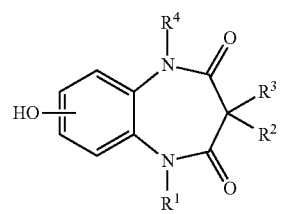

wherein each of $R^1$, $R^2$, $R^3$ and $R^4$, which may be the same or different, represents a hydrogen atom or a lower alkyl group, the process includes deprotecting a protective group ($R^5$) of a compound represented by formula (2),

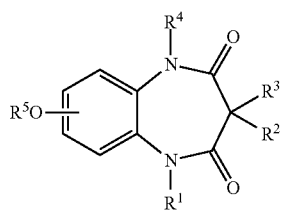

wherein $R^1$, $R^2$, $R^3$ and $R^4$ are as defined above, and $R^5$ represents a protective group of a hydroxy group. The process is an industrially advantageous, simple, and efficient process for producing a key intermediate of a benzo[b][1,4]diazepine-2,4-dione compound, which is a therapeutic medicine for arrhythmia.

5 Claims, No Drawings

(56) References Cited

OTHER PUBLICATIONS

Dan M. Roden, et al., "Current Status of Class III Antiarrhythmic Drug Therapy", The American Journal of Cardiology, Aug. 1993, pp. 44B-49B, vol. 72.

G. Krapivinsky, et al., "The G-Protein-Gated Atrial K+ Channel IKACh is a Heteromultimer of two Inwardly Rectifying K+-Channel Proteins", Nature, Mar. 1995, pp. 135-141, vol. 374.

Gregory J. Amos, et al., "Differences Between Outward Currents of Human Atrial and Subepicardial Ventricular Myocytes", Journal of Physiology, 1996, pp. 31-50, vol. 491.1.

Jamie I. Vandenberg, et al., "HERG K+ Channels: Friend and Foe", Trends in Pharmacological Sciences, May 2001, pp. 240-246, vol. 22, No. 5.

Jianlin Feng, et al., "Antisense Oligodeoxynucleotides Directed Against Kv1.5 mRNA Specifically Inhibit Ultrarapid Delayed Rectifier K+ Current in Cultured Adult Human Atrial Myocytes", Circulation Research, Apr. 1997, pp. 572-579, vol. 80, No. 4.

Richard L. Page, et al., "Drug Therapy for Atrial Fibrillation: Where Do We Go From Here?" Nature Reviews Drug Discovery, Nov. 2005, pp. 899-910, vol. 4.

Stanley Nattel, et al., "Innovative Approaches to Anti-Arrhythmic Drug Therapy", Nature Reviews Drug Discovery, Dec. 2006, pp. 1034-1049, vol. 5.

Yoko Miyasaka et al., "Secular Trends in Incidence of Atrial Fibrillation in Olmsted County, Minnesota, 1980 to 2000, and Implications on the Projections for Future Prevalence", Circulation, Journal of the American Heart Association, Jul. 2006, pp. 119-125, vol. 114.

Z. Wang, et al., "Sustained Depolarization-Induced Outward Current in Human Atrial Myocytes Evidence for a Novel Delayed Rectifier K+ Current Similar to Kv1.5 Cloned Channel Currents", Circulation Research, Dec. 1993, pp. 1061-1076, vol. 73, No. 6.

Final Office Action dated Jun. 14, 2013 issued in U.S. Appl. No. 13/591,361.

Office Action dated Sep. 20, 2013 issued in U.S. Application No. 13/388,442.

Bonsignore et al, European Journal of Medical Chemistry (1994), 29(6), 479-85, Abstract.

Extended European Search Report dated May 22, 2014 in European Application No. 14153418.0.

Lugnier, C. et al., "Analysis of the specificity of inhibitors against some cyclic phosphodiesterases by multiparametric techniques", Die Pharmazie, vol. 47, No. 1, Jan. 1, 1992, pp. 46-49.

Koga, Y. et al, "2(1H)-Quinolinone derivatives as novel anti-arteriostenotic agents showing anti-thrombotic and anti-hyperplastic activities", Bioorganic & Medicinal Chemistry Letters, vol. 8, No. 12, Jun. 16, 1998, pp. 1471-1476.

US 8,796,447 B2

PROCESS FOR PRODUCING BENZO[B][1,4]DIAZEPINE-2,4-DIONE COMPOUND

CROSS REFERENCE TO RELATED APPLICATIONS

This application is a National Stage of International Application No. PCT/JP2010/064040 filed Aug. 20, 2010, claiming priority based on U.S. Provisional Patent Application No. 61/235,988 filed Aug. 21, 2009, the contents of all of which are incorporated herein by reference in their entirety.

TECHNICAL FIELD

The present invention relates to a process for producing a benzo[b][1,4]diazepine-2,4-dione compound that is useful as a production intermediate for medicines, and a starting material compound used in the process.

BACKGROUND ART

Atrial fibrillation (hereinafter referred to as "AF") is the most frequently observed type of arrhythmia in clinical examinations. Although not a lethal arrhythmia, AF causes cardiogenic cerebral embolism, and is therefore recognized as an arrhythmia that greatly affects vital prognoses and QOL. It is known that the onset of AF increases with age, and that repeated AF strokes lead to chronic (serious) AF (Non-patent Literature 1 and 2).

To prevent chronic AF, which causes difficulty in restoring sinus rhythm and increases the risk of cardiogenic cerebral embolism, early defibrillation and subsequent prevention of recurrence (maintenance of the sinus rhythm) are required. Antiarrhythmic drugs (classes I and III) are most commonly used as pharmacotherapy, but these drugs achieve insufficient therapeutic effects, while causing serious side effects such as a proarrhythmic effect (Non-patent Literature 3).

The onset of AF is triggered by atrial premature contraction with underlying causes such as intra-atrial conduction delay, and shortening and heterogeneity of the atrial refractory period (Non-patent Literature 4). It is known that the prolongation of refractory period of atrial muscle can terminate AF (defibrillation), or prevent the occurrence of AF. The action potential duration of the mammalian cardiac muscle is predominantly determined by voltage-dependent K$^+$ channels. It is known that inhibition of the K$^+$ channel prolongs myocardial action potential duration, which results in prolongation of the refractory period (Non-patent Literature 5). The action mechanism of class III antiarrhythmic drugs (e.g., Dofetilide) is to inhibit K$^+$ current ($I_{Kr}$) encoded by HERG. However, since $I_{Kr}$ is present in both the atria and ventricles, such drugs might cause ventricular arrhythmias such as torsades de pointes (Non-patent Literature 6).

K$^+$ current ($I_{kur}$), encoded by Kv1.5, has been identified as a K$^+$ channel that is specifically expressed only in human atria (Non-patent Literature 7, 8 and 9). Muscarine potassium current ($I_{KAch}$), encoded by the two genes known as GIRK1 and GIRK4, is known as a K$^+$ channel specifically expressed in human atria (Non-patent Literature 10). Accordingly, a pharmacologically acceptable substance that selectively blocks the $I_{Kur}$ current (Kv1.5 channel) or the $I_{KAch}$ current (GIRK1/4 channel) can act selectively on the atrial muscle, and is considered effective to exclude the proarrhythmic effect caused by prolonged action potential duration of the ventricular muscle.

The present inventors conducted research to find a compound that can selectively block the Kv1.5 channel or the GIRK1/4 channel. As a result, they found that a novel benzo[b][1,4]diazepine-2,4-dione compound can be used as such a desired compound, and filed a patent application on the compound (Patent Literature 1). Note that Patent Literature 1 was not published on the filing date (Aug. 21, 2009) of the U.S. provisional application No. 61/235,988, which is the priority application of the present international application.

CITATION LIST

Patent Literature

PTL 1: WO2009/104819 published on Aug. 27, 2009 (PCT/JP2009/053623; filed on Feb. 20, 2009)

Non-Patent Literature

NPL 1: The Journal of the American Medical Association, 285, 2370-2375 (2001)
NPL 2: Circulation, 114, 119-123 (2006))
NPL 3: Am. J. Cardiol., 72, B44-B49 (1993)
NPL 4: Nature Reviews Drug Discovery 4, 899-910 (2005)
NPL 5: Nature Reviews Drug Discovery 5, 1034-49 (2006)
NPL 6: Trends Pharmacol. soc., 22, 240-246 (2001)
NPL 7: Cric. Res., 73, 1061-1076 (1993)
NPL 8: J. Physiol., 491, 31-50 (1996)
NPL 9: Cric. Res., 80, 572-579 (1997)
NPL 10: Nature 374, 135-141 (1995)

SUMMARY OF INVENTION

Technical Problem

The novel benzo[b][1,4]diazepine-2,4-dione compound disclosed in Patent Literature 1 is effective as a therapeutic agent for arrhythmia, and is produced through a compound (key intermediate) represented by formula (1),

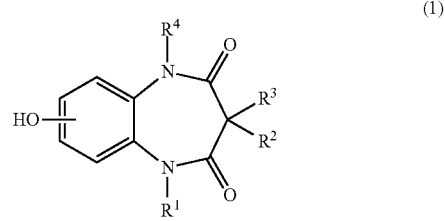

(1)

wherein each of R$^1$, R$^2$, R$^3$ and R$^4$, which may be the same or different, represents a hydrogen atom or a lower alkyl group.

Therefore, a simple and efficient process for producing the compound represented by formula (1) has been desired. An object of the present invention is to provide an industrially advantageous, simple, and efficient process for producing the compound represented by formula (1), and a starting material compound used in the process.

Solution to Problem

The present inventors carried out extensive research regarding the process for producing the compound represented by formula (1) to achieve the above object. As a result, they found that the compound of formula (1) can be obtained in an industrially advantageous, easy, and efficient manner, using easily available 2,4-difluoronitrobenzene, 2,6-difluoronitrobenzene, etc. The present invention was accomplished based on the above finding.

The present invention provides a process for producing a benzo[b][1,4]diazepine-2,4-dione compound and a starting material compound used in this process, which are described in the following Items 1 to 7.

Item 1

A process for producing a compound represented by formula (1),

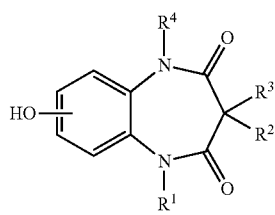

wherein each of $R^1$, $R^2$, $R^3$ and $R^4$, which may be the same or different, represents a hydrogen atom or a lower alkyl group, the process comprising deprotecting a protective group ($R^5$) of a compound represented by formula (2),

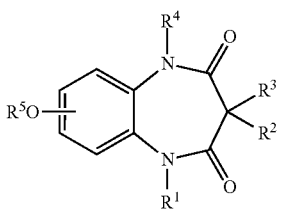

wherein $R^1$, $R^2$, $R^3$ and $R^4$ are as defined above, and $R^5$ represents a protective group of a hydroxy group.

Item 2

The process according to Item 1 for producing a compound represented by formula (1A),

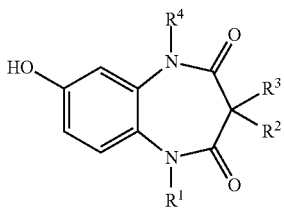

wherein $R^1$, $R^2$, $R^3$ and $R^4$ are as defined above, the process comprising deprotecting a protective group ($R^5$) of a compound represented by formula (2A),

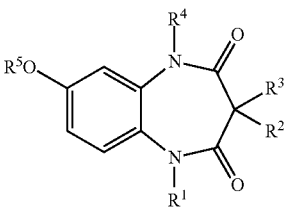

wherein $R^1$, $R^2$, $R^3$, $R^4$ and $R^5$ are as defined above.

Item 3

The process according to Item 1 or 2, wherein $R^5$ is a benzyl group that may be substituted, the process comprising deprotecting the benzyl group that may be substituted by reduction in the presence of a catalytic hydrogenation reducing agent.

Item 4

A compound represented by formula (2),

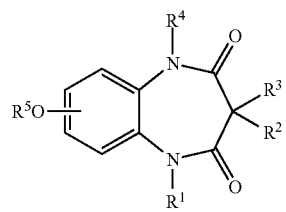

wherein each of $R^1$, $R^2$, $R^3$ and $R^4$, which may be the same or different, represents a hydrogen atom or a lower alkyl group, and $R^5$ represents a protective group of a hydroxy group.

Item 5

A compound represented by formula (2A),

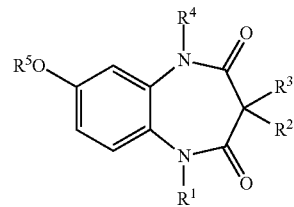

wherein each of $R^1$, $R^2$, $R^3$ and $R^4$, which may be the same or different, represents a hydrogen atom or a lower alkyl group, and $R^5$ represents a protective group of a hydroxy group.

Item 6

The compound according to Item 4, which is represented by formula (2a),

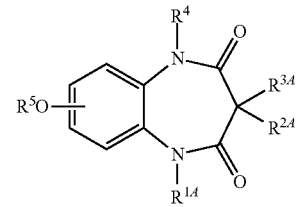

wherein each of $R^{1A}$, $R^{2A}$ and $R^{3A}$, which may be the same or different, represents a lower alkyl group, and $R^4$ and $R^5$ are as defined above.

Item 7

A process for producing a compound represented by formula (2h),

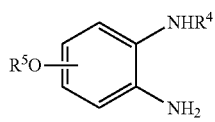
(2h)

wherein each of $R^2$, $R^3$, and $R^4$, which may be the same or different, represents a hydrogen atom or a lower alkyl group, and $R^5$ represents a protective group of a hydroxy group, the process comprising reacting a compound represented by formula (19),

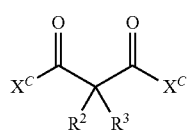
(19)

wherein $R^4$ and $R^5$ are as defined above, or a salt thereof, and a compound represented by formula (14), (14)

wherein $R^2$ and $R^3$ are as defined above, and $X^c$, which may be the same or different, represents a halogen atom.

Advantageous Effects of Inventions

According to the production process of the present invention, the benzo[b][1,4]diazepine-2,4-dione compound represented by formula (1), which has a hydroxy group on a benzene ring, can be produced in an industrially advantageous, simple, and efficient manner.

DESCRIPTION OF EMBODIMENTS

The process for producing the benzo[b][1,4]diazepine-2,4-dione compound represented by formula (1) of the present invention is explained in detail below.

The reaction that produces the compound represented by formula (1) from the compound represented by formula (2) can be carried out by deprotecting the protective group ($R^5$) in a suitable solvent.

Reaction scheme 1

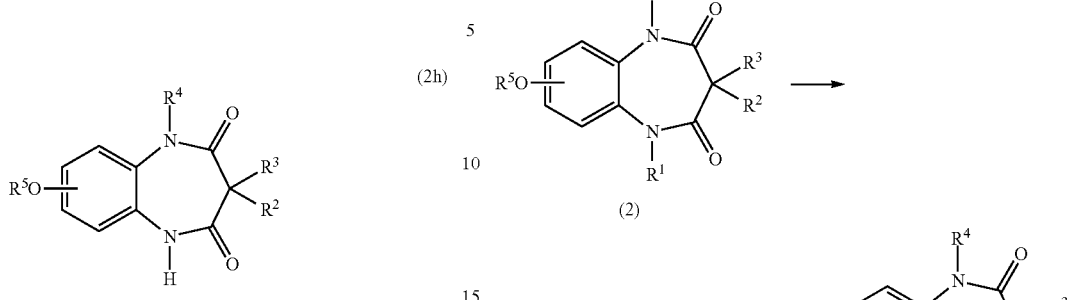

In the formula, $R^1$, $R^2$, $R^3$, $R^4$ and $R^5$ are as defined above.

Examples of the lower alkyl group represented by $R^1$, $R^2$, $R^3$, or $R^4$ include straight or branched $C_{1-6}$ alkyl groups such as methyl, ethyl, n-propyl, isopropyl, n-butyl, isobutyl, tert-butyl, sec-butyl, n-pentyl, neopentyl, n-hexyl and isohexyl, and preferably $C_{1-4}$ alkyl groups such as methyl, ethyl, n-propyl, isopropyl, n-butyl and isobutyl.

The protective group represented by $R^5$ for the hydroxy group is, for example, a benzyl group that may be substituted.

Examples of the substituent of the benzyl group that may be substituted include lower alkyl groups, halogen atoms, cyano groups, lower alkoxy groups, nitro groups, phenyl groups, acyl groups, and the like. The benzene ring of the benzyl group may be substituted with at least 1 to 5 (particularly 1 to 3) substituents selected from these groups.

The lower alkyl group can be selected from the lower alkyl groups represented by $R^1$, $R^2$, $R^3$ and $R^4$.

Examples of the halogen atom include fluorine, chlorine, bromine and iodine.

Examples of the lower alkoxy group include straight or branched $C_{1-6}$ alkoxy groups such as methoxy, ethoxy, propoxy, isopropoxy and n-butoxy. In particular, $C_{1-4}$ alkoxy groups are preferable.

Examples of the acyl group include lower alkanoyl groups (for example, $C_{1-6}$ alkanoyl groups) such as formyl, acetyl, propionyl, hexanoyl and pivaloyl; lower alkoxycarbonyl groups (for example, $C_{1-6}$ alkoxycarbonyl groups) such as methoxycarbonyl, ethoxycarbonyl, tert-butoxycarbonyl, tert-pentyloxycarbonyl and hexyloxycarbonyl; aroyl groups such as benzoyl, toluoyl and naphthoyl; aryl lower alkoxycarbonyl groups (for example, aryl $C_{1-6}$ alkoxycarbonyl groups) that may be substituted with suitable substituents, such as benzyloxycarbonyl, phenethyloxycarbonyl, p-nitrobenzyloxycarbonyl; and the like.

Preferable examples of the benzyl group that may be substituted include benzyl, p-methoxybenzyl, 3,4-dimethoxybenzyl, 2,6-dimethoxybenzyl, o-nitrobenzyl, p-nitrobenzyl, chlorobenzyl, fluorobenzyl, 2,6-dichlorobenzyl, 2,4-dichlorobenzyl, 2,6-difluorobenzyl, p-cyanobenzyl, p-phenylbenzyl, p-acetylbenzyl, and the like.

In the compound represented by formula (1), the binding position of the hydroxy group on the benzene ring is not particularly limited. Examples of the compound represented by formula (1) include compounds represented by the following formulae (1A) to (1D), and preferably the compounds represented by formulae (1A) and (1B). In the formula, the wavy lines indicate the abbreviation of the structural formulae.

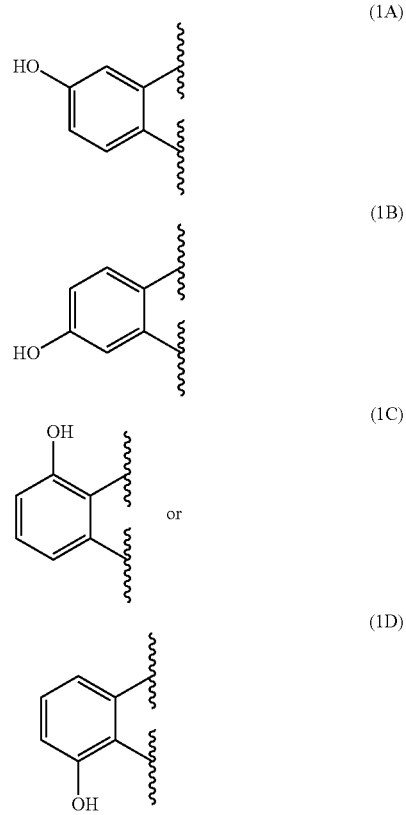

As a preferable example of the reaction scheme 1, reaction scheme 1A is shown below.

Reaction scheme 1A

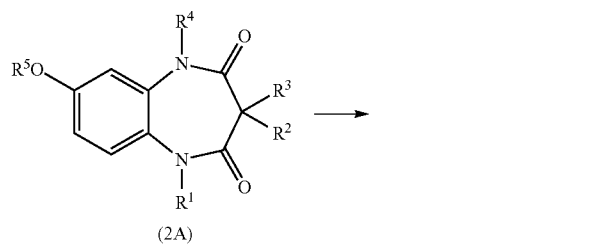

In the formula, $R^1$, $R^2$, $R^3$, $R^4$ and $R^5$ are as defined above.

The case where $R^5$ is a benzyl group, which is the typical example of this reaction, is explained below. The reaction that produces the compound represented by formula (1) from the compound represented by formula (2) can be carried out by performing reduction (debenzylation) in a suitable solvent in the presence of a catalytic hydrogenation reducing agent.

The solvent is not particularly limited, as long as it does not adversely affect the reduction reaction. Examples of the solvent include carboxylic acids such as formic acid and acetic acid; ethers such as dioxane, tetrahydrofuran, diethyl ether, diethylene glycol dimethyl ether and ethylene glycol dimethyl ether; lower alcohols (for example, $C_{1-6}$ alcohols) such as methanol, ethanol and isopropanol; hydrocarbons such as n-hexane and cyclohexane; esters such as ethyl acetate and methyl acetate; aprotic polar solvents such as N,N-dimethylformamide; aromatic hydrocarbons such as benzene, toluene and xylene; and mixture solvents thereof, and preferably $C_{1-3}$ alcohols such as methanol, ethanol and isopropanol.

Examples of the catalytic hydrogenation reducing agent include palladium black, palladium carbon, palladium hydroxide carbon, platinum carbon, platinum, platinum black, platinum oxide, copper chromite, Raney nickel, and the like.

The amount of the catalytic hydrogenation reducing agent used is generally 0.1 to 40 wt %, and preferably 1 to 20 wt %, relative to the compound represented by formula (2).

The reaction can be generally performed in a hydrogen atmosphere at 1 to 20 atm, preferably 1 to 10 atm, and more preferably 1 to 5 atm. The reaction is generally performed at −20 to 150° C., and preferably 0 to 100° C. The reaction is generally completed in about 0.5 to 100 hours. In the reaction, acids such as hydrochloric acid, may be added.

In the reaction scheme 1, the determined protective group ($R^5$) as described above is used as a protective group of the hydroxy group on the benzene ring. Thereby, in the process of producing the compound represented by formula (2), the hydroxy group on the benzene ring can be suitably protected, and then deprotected under mild conditions to efficiently produce the compound represented by formula (1). Among the aforementioned protective groups ($R^5$), a benzyl group that may be substituted is particularly preferable.

The compound represented by formula (2) includes the compounds represented by the following formulae (2a) to (2i). The compounds represented by formulae (2a) to (2i) are converted into the corresponding compounds (1a) to (1i) each having a phenolic hydroxy group by the deprotection reaction.

Next, the processes of producing the compounds represented by formulae (2a) to (2i) are explained below.

The compounds represented by formulae (2a) to (2c) can be produced, for example, by the process described in the reaction scheme 2.

Reaction scheme 2

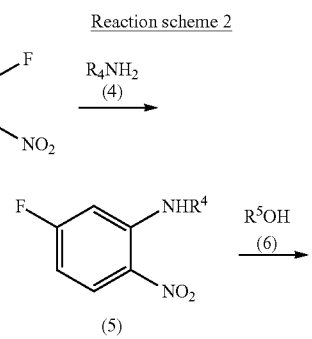

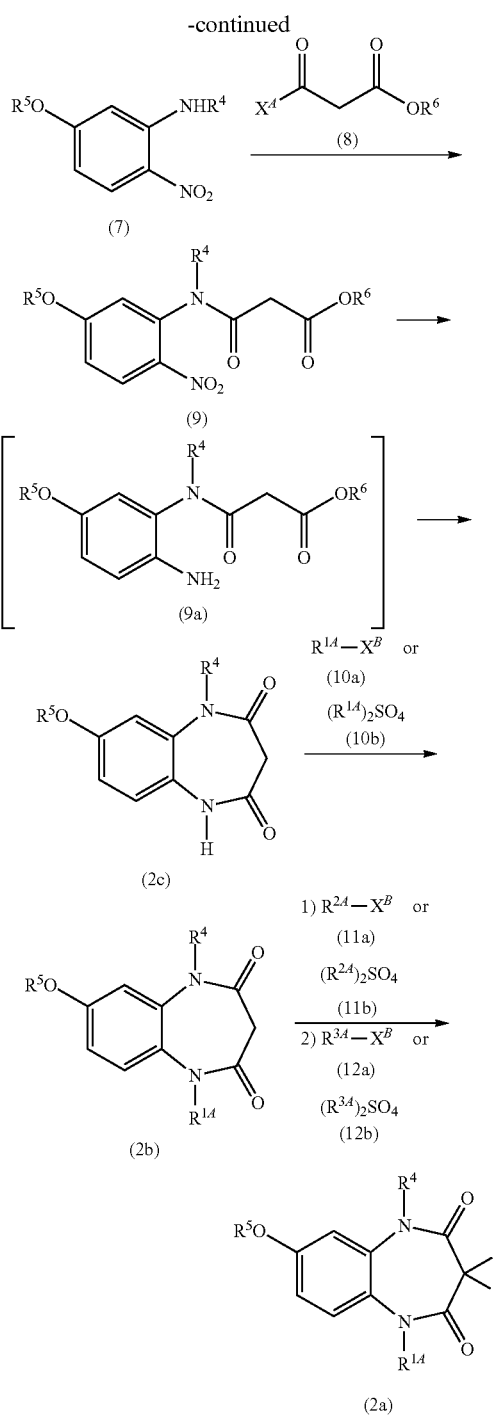

In the formula, $R^{1A}$, $R^{2A}$, $R^{3A}$, $R^4$ and $R^5$ are as defined above, $R^6$ represents a lower alkyl group, $X^A$ represents a halogen atom, and $X^B$ represents a leaving group.

Examples of the lower alkyl group represented by $R^{1A}$, $R^{2A}$, or $R^{3A}$ include straight or branched $C_{1-6}$ alkyl groups such as methyl, ethyl, n-propyl, isopropyl, n-butyl, isobutyl, tert-butyl, sec-butyl, n-pentyl, neopentyl, n-hexyl and isohexyl; and preferably $C_{1-4}$ alkyl groups such as methyl, ethyl, n-propyl, isopropyl, n-butyl and isobutyl.

Examples of the lower alkyl group represented by $R^6$ include straight or branched $C_{1-6}$ alkyl groups such as methyl, ethyl, n-propyl, isopropyl, n-butyl, isobutyl, tert-butyl, sec-butyl, n-pentyl, neopentyl, n-hexyl and isohexyl. In particular, $C_{1-3}$ alkyl groups such as methyl, ethyl and isopropyl are preferable.

Examples of the halogen atom represented by $X^A$ include fluorine, chlorine, bromine and iodine, and preferably chlorine.

Examples of the leaving group represented by $X^B$ include halogen atoms (for example, fluorine, chlorine, bromine, iodine, etc.) and organic sulfonyloxy groups (for example, p-toluenesulfonyloxy, methanesulfonyloxy, trifluoromethanesulfonyloxy, nonafluorobutanesulfonyloxy, etc.), and preferably iodine and p-toluenesulfonyloxy.

Compound (3)→(5):

The reaction of the compound represented by formula (3) and the compound represented by formula (4) can be performed in a suitable solvent.

Examples of the solvent include water; ethers such as dioxane, tetrahydrofuran, diethyl ether, diethylene glycol dimethyl ether and ethylene glycol dimethyl ether; lower alcohols (for example $C_{1-6}$ alcohols) such as methanol, ethanol and isopropanol; aromatic hydrocarbons such as benzene, toluene and xylene; and mixture solvents thereof. Preferable examples include water; $C_{1-3}$ alcohols such as methanol and ethanol, aromatic hydrocarbons such as toluene and xylene, and mixture solvents thereof.

The proportion of the compound represented by formula (3) and the compound represented by formula (4) is such that the latter is used in an amount of 0.5 to 10 mol, preferably 0.8 to 10 mol, and more preferably 1.8 to 5.0 mol, per mol of the former.

The temperature of the reaction is generally −20 to 150° C., and preferably −20 to 100° C. The reaction is generally completed in about 0.5 to 10 hours.

Compound (5)→(7):

The reaction of the compound represented by formula (5) and the compound represented by formula (6) can be carried out in a suitable solvent in the presence of a basic compound, optionally in the presence of a phase transfer catalyst.

Examples of the solvent include water; ethers such as dioxane, tetrahydrofuran, diethyl ether, diethylene glycol dimethyl ether and ethylene glycol dimethyl ether; aromatic hydrocarbons such as benzene, toluene and xylene; halogenated hydrocarbons such as dichloromethane, dichloroethane, chloroform and carbon tetrachloride; lower alcohols (for example, $C_{1-6}$ alcohols) such as methanol, ethanol and isopropanol; ketones such as acetone and methyl ethyl ketone; polar solvents such as dimethylformamide (DMF), dimethylacetamide (DMA), dimethyl sulfoxide (DMSO), hexamethylphosphoric triamide and acetonitrile; and mixtures thereof.

The basic compound can be selected from a wide variety of known inorganic and organic bases. Examples of the inorganic bases include alkali metal hydroxides such as sodium hydroxide, potassium hydroxide, cesium hydroxide and lithium hydroxide; alkali metal carbonates such as sodium carbonate, potassium carbonate, cesium carbonate, lithium carbonate, lithium hydrogen carbonate, sodium hydrogen carbonate and potassium hydrogen carbonate; alkali metals such as sodium and potassium; alkali metal amides such as sodium amide; alkali metal hydrides such as sodium hydride and potassium hydride; and the like. Examples of the organic bases include alkali metal alcoholates such as sodium methoxide, sodium ethoxide, sodium tert-butoxide, potassium methoxide, potassium ethoxide, potassium tert-butoxide; triethylamine; tripropylamine; pyridine; quinoline; 1,5-diazabicyclo[4.3.0]non-5-ene (DBN); 1,8-diazabicyclo[5.4.0]undec-7-ene (DBU); 1,4-diazabicyclo[2.2.2]octane (DABCO); and the like. Such basic compounds can be used singly, or as a mixture of two or more.

The amount of the basic compound used is generally 0.5 to 10 mol, and preferably 0.5 to 6 mol, per mol of the compound represented by formula (5).

The proportion of the compound represented by formula (5) and the compound represented by formula (6) used is such that the latter is 0.5 to 10 mol, preferably 0.8 to 5.0 mol, and more preferably 0.9 to 3.0 mol, per mol of the former.

The phase transfer catalyst can be used to promote the reaction, and examples thereof include quaternary ammonium salts, phosphonium salts, pyridinium salts, and the like.

Examples of the quaternary ammonium salts include quaternary ammonium salts in which groups selected from the group consisting of straight or branched $C_{1-18}$ alkyl groups, phenyl alkyl groups in which the alkyl moiety is a straight or branched $C_{1-6}$ alkyl group, and phenyl groups, are bonded to a nitrogen atom.

Examples of the quaternary ammonium salts include tetrabutyl ammonium chloride, tetrabutyl ammonium bromide, tetrabutyl ammonium fluoride, tetrabutyl ammonium iodide, tetrabutyl ammonium hydroxide, tetrabutyl ammonium hydrogen sulfite, tetrabutyl ammonium hydrogen sulfate, tributylmethyl ammonium chloride, tributylbenzyl ammonium chloride, tetrapentyl ammonium chloride, tetrapentyl ammonium bromide, tetrahexyl ammonium chloride, benzyldimethyloctyl ammonium chloride, methyl trihexyl ammonium chloride, benzyldimethyl octadecanyl ammonium chloride, methyltridecanyl ammonium chloride, benzyltripropyl ammonium chloride, benzyl triethyl ammonium chloride, phenyl triethyl ammonium chloride, tetraethyl ammonium chloride, tetramethyl ammonium chloride, and the like.

Examples of the phosphonium salts include phosphonium salts in which straight or branched $C_{1-18}$ alkyl groups are bonded to a phosphorus atom. Specific examples of the phosphonium salts include tetrabutyl phosphonium chloride, and the like.

Examples of the pyridinium salts include pyridinium salts in which a $C_{1-18}$ straight or branched alkyl group is bonded to a nitrogen atom. Specific examples of the pyridinium salts include 1-dodecanyl pyridinium chloride, and the like.

The phase transfer catalysts can be used singly, or as a mixture of two or more.

The amount of the phase transfer catalyst is generally 0.01 to 1 mol, and preferably 0.02 to 0.5 mol, per mol of the compound represented by formula (5).

The reaction is generally performed at −10 to 150° C., and preferably 0 to 120° C.; and is generally completed in 0.5 to 80 hours. If necessary, conversion into salts such as hydrochloride, ½ sulfate, p-toluenesulfonate, etc., using a known salt-forming method is possible.

Compound (7)→(9):

The reaction of the compound represented by formula (7) or a salt thereof and the compound represented by formula (8) can be performed in a suitable solvent.

Examples of the solvent include ethers such as dioxane, tetrahydrofuran, diethyl ether, diethylene glycol dimethyl ether and ethylene glycol dimethyl ether; aromatic hydrocarbons such as benzene, toluene and xylene; halogenated hydrocarbons such as dichloromethane, dichloroethane, chloroform and carbon tetrachloride; ketones such as acetone and methyl ethyl ketone; polar solvents such as dimethylformamide (DMF), dimethylacetamide (DMA), dimethyl sulfoxide (DMSO), hexamethylphosphoric triamide and acetonitrile, and mixture solvents thereof, and preferably aromatic hydrocarbons such as toluene and xylene.

The amount of the compound represented by Formula (8) is generally 0.5 to 2 mol, preferably 0.7 to 1.3 mol, and more preferably 0.9 to 1.2 mol, per mol of the compound represented by formula (7).

The reaction is generally performed at 0 to 150° C., and preferably at 0 to 120° C., and is generally completed in 1 to 80 hours.

Compound (9)→(9a):

The reaction that produces the compound represented by formula (9a) from the compound represented by formula (9) can be carried out in a suitable solvent in the presence of a catalytic hydrogenation reducing agent.

The solvent is not particularly limited as long as it does not adversely affect the reduction reaction. Examples of the solvent include carboxylic acids such as formic acid and acetic acid; ethers such as dioxane, tetrahydrofuran, diethyl ether, diethylene glycol dimethyl ether and ethylene glycol dimethyl ether; lower alcohols (for example, $C_{1-6}$ alcohols) such as methanol, ethanol and isopropanol; hydrocarbons such as n-hexane and cyclohexane; esters such as ethyl acetate and methyl acetate; aprotic polar solvents such as N,N-dimethylformamide; aromatic hydrocarbons such as benzene, toluene and xylene; and mixture solvents thereof, and preferably $C_{1-3}$ alcohols such as methanol, ethanol and isopropanol.

Examples of the catalytic hydrogenation reducing agent include palladium black, palladium carbon, palladium hydroxide carbon, platinum carbon, platinum, platinum black, platinum oxide, copper chromite, Raney nickel, and the like.

The amount of the catalytic hydrogenation reducing agent used is generally 0.1 to 40 wt %, and preferably 1 to 20 wt %, relative to the compound represented by formula (9).

It is preferable to add a substance (i.e., poisoning substance) capable of reducing the catalytic activity of the catalytic hydrogenation reducing agent. Examples of the poisoning substance include sulfides such as diphenyl sulfide and dimethyl sulfide; dipyridyl; ethylenediamine; and the like, and preferably diphenyl sulfide. By these poisoning substances, even when $R^5$ in the compound represented by formula (9) is a benzyl group, the nitro group can be selectively reduced to an amino group without debenzylation.

When the poisoning substance is used, the amount of the poisoning substance is generally 0.0001 to 0.2 mol, and preferably 0.001 to 0.1 mol, per mol of the compound represented by formula (9).

The reaction can be generally performed in a hydrogen atmosphere at 0.5 to 20 atm, preferably 1 to 10 atm, and more preferably 1 to 5 atm. The reaction is generally performed at −20 to 50° C., and preferably −10 to 40° C. The reaction is generally completed in about 0.5 to 100 hours.

The compound represented by formula (9a) can be subjected to the subsequent ring-closing reaction in its crude product form.

Compound (9a)→(2c):

The reaction that produces the compound represented by formula (2c) from the compound represented by formula (9a) can be carried out in a suitable solvent, in the presence of a basic compound.

The solvent is not particularly limited, as long as it does not adversely affect the ring-closing reaction. Examples thereof include ethers such as dioxane, tetrahydrofuran, diethyl ether, diethylene glycol dimethyl ether, ethylene glycol dimethyl ether; aromatic hydrocarbons such as benzene, toluene and xylene; esters such as ethyl acetate and methyl acetate; aprotic polar solvents such as N,N-dimethylformamide; and mixture solvents thereof; and preferably aromatic hydrocarbons such as toluene and xylene.

The basic compound can be selected from a wide variety of known inorganic and organic bases. Examples of the inorganic bases include alkali metal hydroxides such as sodium hydroxide, potassium hydroxide, cesium hydroxide and lithium hydroxide; alkali metal carbonates such as sodium carbonate, potassium carbonate, cesium carbonate, lithium carbonate, lithium hydrogen carbonate, sodium hydrogen carbonate and potassium hydrogen carbonate; alkali metals such as sodium and potassium; sodium amide; sodium hydride; potassium hydride; potassium bis(trimethylsilyl)amide; and the like. Examples of the organic bases include alkali metal alcoholates such as sodium methoxide, sodium ethoxide, sodium tert-butoxide, potassium methoxide, potassium ethoxide, potassium tert-butoxide; triethylamine; tripropylamine; pyridine; quinoline; 1,5-diazabicyclo[4.3.0]non-5-ene (DBN); 1,8-diazabicyclo[5.4.0]undec-7-ene (DBU); 1,4-diazabicyclo[2.2.2]octane (DABCO); and the like. Such basic compounds can be used singly, or as a mixture of two or more.

The amount of the basic compound is generally 0.001 to 10 mol, and preferably 0.2 to 2 mol, per mol of the compound represented by formula (9a). In particular, when a basic compound such as sodium tert-butoxide, potassium bis(trimethylsilyl)amide, potassium hydroxide, or potassium carbonate is used, the amount of the basic compound is about 0.1 to 0.8 mol (catalytic content) per mol of the compound (9a).

Compound (2c)→(2b):

The reaction of the compound represented by formula (2c) and the compound represented by formula (10a) or (10b) (hereinbelow referred to as a lower alkylating agent (10)) can be carried out without using a solvent or in a general inert solvent, in the presence of a basic compound, optionally in the presence of a phase transfer catalyst.

Examples of the inert solvent include water; ethers such as dioxane, tetrahydrofuran, diethyl ether, diethylene glycol dimethyl ether and ethylene glycol dimethyl ether; aromatic hydrocarbons such as benzene, toluene and xylene; halogenated hydrocarbons such as dichloromethane, dichloroethane, chloroform and carbon tetrachloride; lower alcohols (for example, $C_{1-6}$ alcohols) such as methanol, ethanol and isopropanol; ketones such as acetone and methyl ethyl ketone; polar solvents such as dimethylformamide (DMF), dimethylacetamide (DMA), dimethyl sulfoxide (DMSO), hexamethylphosphoric triamide and acetonitrile; and mixtures thereof.

The basic compound can be selected from a wide variety of known compounds. Examples thereof include inorganic bases including alkali metal hydroxides such as sodium hydroxide, potassium hydroxide, cesium hydroxide and lithium hydroxide; alkali metal carbonates such as sodium carbonate, potassium carbonate, cesium carbonate, lithium carbonate, lithium hydrogen carbonate, sodium hydrogen carbonate and potassium hydrogen carbonate; alkali metals such as sodium and potassium; sodium amide; sodium hydride; potassium hydride; and the like; and organic bases including alkali metal alcoholates such as sodium methoxide, sodium ethoxide, sodium tert-butoxide, potassium methoxide, potassium ethoxide, potassium tert-butoxide; triethylamine; tripropylamine; pyridine; quinoline; 1,5-diazabicyclo[4.3.0]non-5-ene (DBN); 1,8-diazabicyclo[5.4.0]undec-7-ene (DBU); 1,4-diazabicyclo[2.2.2]octane (DABCO); and the like. Such basic compounds can be used singly, or as a mixture of two or more.

The amount of the basic compound used is generally 0.5 to 10 mol, and preferably 0.5 to 6 mol, per mol of the compound represented by formula (2c).

The phase transfer catalyst can be used to promote the reaction. For example, the phase transfer catalyst (e.g., quaternary ammonium salts, phosphonium salts, pyridinium salts, etc.) used in the step in which the compound (5) is converted into the compound (7) in the reaction scheme 2 can be used. The amount of the phase transfer catalyst used is generally 0.01 to 1 mol, and preferably 0.01 to 0.5 mol, per mol of the compound (2c).

The above reaction can be performed by adding, if necessary, an alkali iodide compound such as potassium iodide and sodium iodide as a reaction promoter to the inside of the reaction system. The amount of the alkali iodide compound used is generally 0.1 to 10 mol, and preferably 0.8 to 3.0 mol, per mol of the compound (2c).

The proportion of the compound represented by formula (2c) and the lower alkylating agent (10) is such that the amount of the latter is at least 1 mol, preferably 1 to 1.5 mol, and more preferably 1 to 1.3 mol, per mol of the former.

The reaction is generally performed at −20 to 100° C., and preferably 0 to 80° C.; and is generally completed in about 0.5 to 80 hours.

Compound (2b)→(2a):

The reaction of the compound represented by formula (2b) and the compound represented by formula (11a) or (11b) (hereinbelow referred to as a lower alkylating agent (11)), and the reaction of the compound obtained by the aforementioned reaction and the compound represented by formula (12a) or (12b) (hereinbelow referred to as a lower alkylating agent (12)) can be carried out under the same conditions as the reaction of the compound represented by formula (2c) and the lower alkylating agent (10) in the reaction scheme 2.

When the lower alkyl group ($R^{2,4}$) in the lower alkylating agent (11) is different from the lower alkyl group ($R^{3,4}$) in the lower alkylating agent (12), the lower alkylating agent (11) in an amount of at least 0.5 mol (particularly 0.5 to 1.5 mol), and then the lower alkylating agent (12) in an amount of at least 1 mol (particularly 1 to 3 mol), per mol of the compound represented by formula (2b) can be reacted stepwise.

When the lower alkyl group ($R^{2,4}$) in the lower alkylating agent (11) is the same as the lower alkyl group ($R^{3,4}$) in the lower alkylating agent (12), the lower alkylating agent (11) and/or (12) in a total amount of at least 2 mol (particularly 2 to 5 mol) per mol of the compound represented by formula (2b) can be reacted in one step.

The compounds represented by formulae (2a) to (2c) can be produced through the steps described in the reaction scheme 2.

The compounds represented by formulae (2d) and (2e) can be produced, for example, by the process described in the reaction scheme 3.

Reaction scheme 3

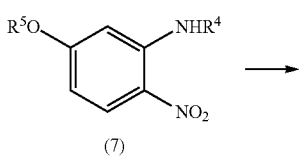

(7)

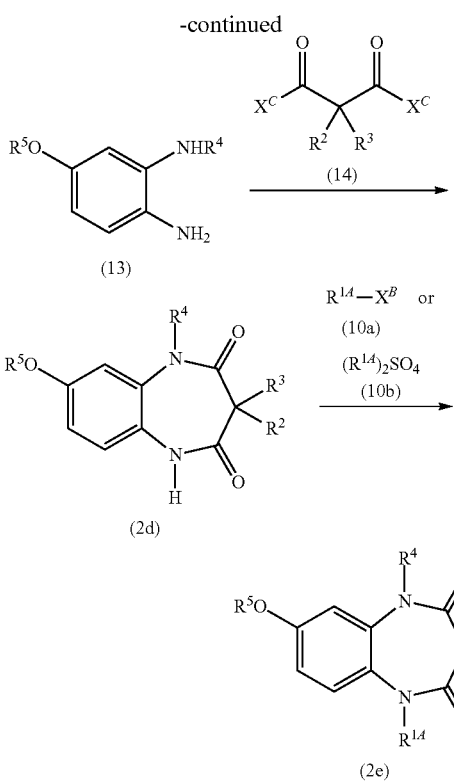

In the formula, $R^{14}$, $R^2$, $R^3$, $R^4$, $R^5$ and $X^B$ are as defined above, and $X^C$ is the same or different, and represents a halogen atom.

Examples of the halogen atom represented by $X^C$ include fluorine, chlorine, bromine and iodine, and preferably chlorine.

Compound (7)→(13):

The reaction that produces the compound represented by formula (13) from the compound represented by formula (7) can be performed under the same conditions as the reaction that produces the compound represented by formula (9a) from the compound represented by formula (9) in the above reaction, if necessary, 2. The resulting compound represented by formula (13) can be converted into a salt such as hydrochloride, sulphate, and p-toluenesulfonate, using a known salt-forming method. By converting the compound into the salt, the phenylenediamine compound represented by formula (13), which is generally unstable, can be stably obtained.

Compound (13)→(2d):

The reaction of the compound represented by formula (13) and the compound represented by formula (14) can be performed under the same conditions as the reaction that produces the compound represented by formula (9) from the compound represented by formula (7) in the above reaction scheme 2.

Specifically, the reaction of the compound represented by formula (13) or a salt thereof and the compound represented by formula (14) can be performed in a suitable solvent.

Examples of the solvent include ethers such as dioxane, tetrahydrofuran, diethyl ether, diethylene glycol dimethyl ether, and ethylene glycol dimethyl ether; aromatic hydrocarbons such as benzene, toluene, and xylene; halogenated hydrocarbons such as dichloromethane, dichloroethane, chloroform, and carbon tetrachloride; ketones such as acetone and methyl ethyl ketone; polar solvents such as dimethylformamide (DMF), dimethylacetamide (DMA), dimethyl sulfoxide (DMSO), hexamethylphosphoric triamide, and acetonitrile, and mixture solvents thereof, and preferably aromatic hydrocarbons such as toluene and xylene.

The amount of the compound represented by formula (14) used is generally 0.5 to 1.5 mol, preferably 0.7 to 1.3 mol, and more preferably 0.8 to 1.2 mol per mol of the compound represented by formula (13).

The reaction is generally performed at 0 to 150° C., and preferably 0 to 120° C., and is generally completed in 1 to 80 hours.

Compound (2d)→(2e):

The reaction of the compound represented by formula (2d) and the lower alkylating agent (10) can be performed under the same reaction conditions as the reaction that produces the compound represented by formula (2b) from the compound represented by formula (2c) in the above reaction scheme 2.

The compound represented by formula (2d) or (2e) can be produced through the steps described in the above reaction scheme 3.

The compounds represented by formula (2f) and (2g) can be, for example, produced by the process described in the above reaction scheme 4.

Reaction scheme 4

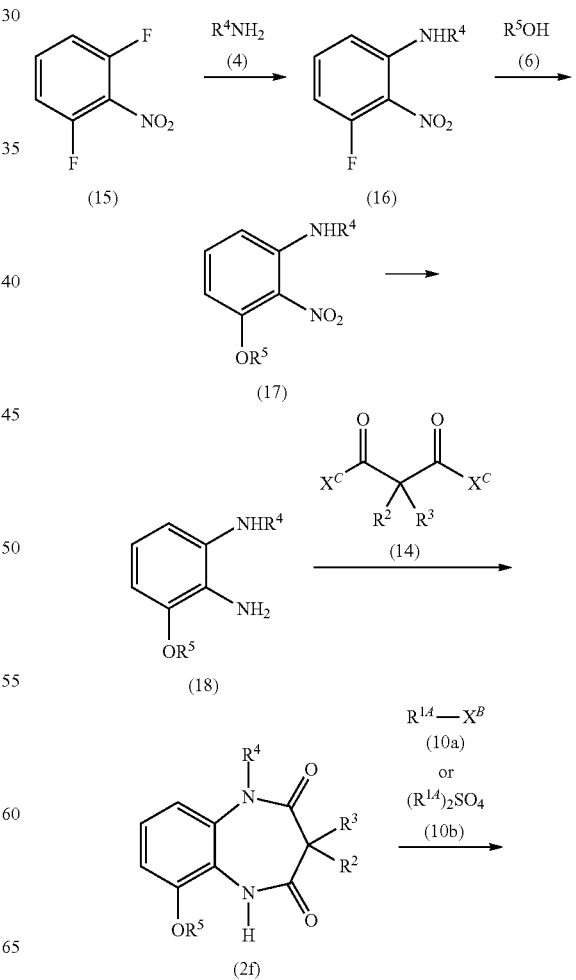

-continued

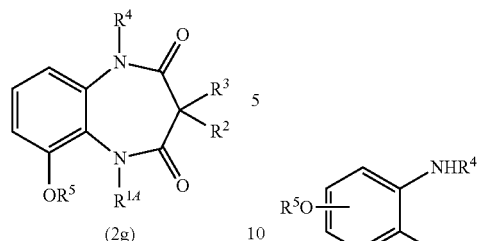

(2g)

In the formula, $R^{1A}$, $R^2$, $R^3$, $R^4$, $R^5$, $X^B$ and $X^C$ are as defined above.

Compound (15)→(16)

The reaction of the compound represented by formula (15) and the compound represented by formula (4) can be performed under the same conditions as the reaction that produces the compound represented by formula (5) from the compound represented by formula (3) in the above reaction scheme 2.

Compound (16)→(17):

The reaction of the compound represented by formula (16) and the compound represented by formula (6) can be performed under the same conditions as the reaction that produces the compound represented by formula (7) from the compound represented by formula (5) in the above reaction scheme 2.

Compound (17)→(18)

The reaction that produces the compound represented by formula (18) from the compound represented by formula (17) can be performed under the same conditions as the reaction that produces the compound represented by formula (13) from the compound represented by formula (7) in the above reaction scheme 3. The resulting compound represented by formula (18) can be, if necessary, converted into a salt such as hydrochloride, sulphate and p-toluenesulfonate, using a known salt-forming method. By converting the compound into the salt, the phenylenediamine compound represented by formula (18), which is generally unstable, can be stably obtained.

Compound (18)→(2f):

The reaction of the compound represented by formula (18) and the compound represented by formula (14) can be performed under the same conditions as the reaction that produces the compound represented by formula (2d) from the compound represented by formula (13) in the above reaction scheme 3.

Compound (2f)→(2g):

The reaction of the compound represented by formula (2f) and the lower alkylating agent represented by formula (10) can be performed under the same conditions as the reaction that produces the compound represented by formula (2b) from the compound represented by formula (2c) in the above reaction scheme 2.

The compounds represented by formulae (2h) and (2i) can be produced, for example, by the process described in the above reaction scheme 5.

Reaction scheme 5

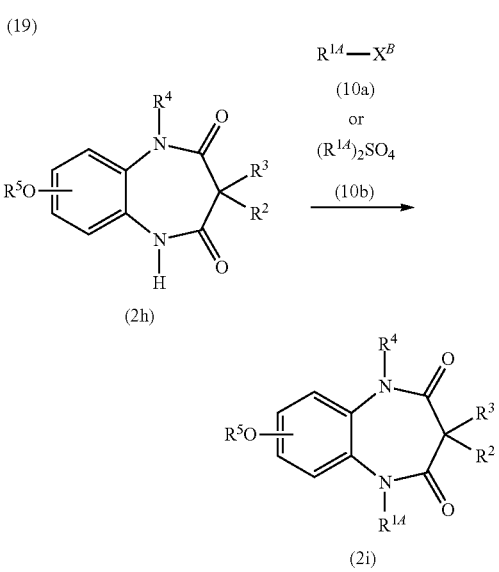

In the formula, $R^{1A}$, $R^2$, $R^3$, $R^4$, $R^5$, $X^B$ and $X^C$ are as defined above.

Compound (19)→(2h):

The reaction of the compound represented by formula (19) and the compound represented by formula (14) can be performed under the same conditions as the reaction that produces the compound represented by formula (2d) from the compound represented by formula (13) in the above reaction scheme 3.

Compound (2h)→(2i)

The reaction of the compound represented by formula (2h) and the lower alkylating agent represented by formula (10) can be performed under the same conditions as the reaction that produces the compound represented by formula (2b) from the compound represented by formula (2c) in the above reaction scheme 2.

In each step of the above reaction schemes, a target compound can be obtained from a reaction mixture after the completion of the reaction by using a known isolation operation (e.g., filtration, concentration, extraction, etc.) and known purifying means (e.g., column chromatography, recrystallization, etc.).

EXAMPLES

Hereinafter, the present invention will be explained with reference to Examples; however, the invention is not limited thereto.

Example 1

Synthesis of 5-fluoro-N-methyl-2-nitroaniline

An aqueous solution of 40% methyl amine (61 mL, 0.71 mol) was added dropwise to a methanol solution (200 mL) of 2,4-difluoronitrobenzene (46.7 g, 0.29 mol) under ice cooling, and the mixture was stirred for 1 hour under the same temperature. The reaction solution was poured into ice water. Precipitated crystals were collected by filtration, followed by washing with water. The resulting crystals were dried at 50° C., thereby obtaining 47.6 g of a yellow, powdery target compound (yield: 95%).

$^1$H-NMR (CDCl$_3$) δppm: 3.00 (3H, d, J=5.1 Hz), 6.3-6.4 (1H, m), 6.47 (1H, dd, J=11.4 Hz, 2.6 Hz), 8.0-8.3 (1H, br), 8.1-8.3 (1H, m)

Example 2

Synthesis of 5-benzyloxy-N-methyl-2-nitroaniline

Benzyl alcohol (49.6 mL, 0.48 mol), tetrabutyl ammonium chloride (6.66 g, 24.0 mmol) and potassium carbonate (40.0 g, 0.29 mol) were added to a toluene solution (200 mL) of 5-fluoro-N-methyl-2-nitroaniline (40.8 g, 0.24 mol), and the mixture was heated under reflux for 3.5 hours. The reaction solution was cooled, and 100 mL of water was added thereto. Thereafter, the mixture was stirred for 1 hour at 60 to 70° C. After the mixture was stirred under ice cooling for 30 minutes, precipitated crystals were collected by filtration. The resulting crystals were washed with water, and dried at 50° C., thereby obtaining 57.1 g of an orange, powdery target compound (yield: 92%).

$^1$H-NMR (CDCl$_3$) δppm: 2.98 (3H, d, J=5.1 Hz), 5.14 (2H, s), 6.22 (1H, d, J=2.5 Hz), 6.32 (1H, dd, J=9.5 Hz, 2.5 Hz), 7.3-7.5 (5H, m), 8.15 (1H, d, J=9.5 Hz), 8.26 (1H, brs)

Example 3

Benzyl alcohol (0.93 mL, 9 mmol) and potassium carbonate (1.24 g, 9 mmol) were added to a N,N-dimethyl formamide solution (5 mL) of 5-fluoro-N-methyl-2-nitroaniline (510 mg, 3 mmol). The mixture was stirred at 60-70° C. for 8 hours. The reaction solution was cooled, then water was added thereto, and precipitated crystals were collected by filtration. The resulting crystals were washed with water, and dried at 50° C., thereby obtaining 680 mg of orange, powdery 5-benzyloxy-N-methyl-2-nitroaniline (yield: 88%).

Example 4

Sodium t-butoxide (865 mg, 9 mmol) was added to a N,N-dimethylformamide (5 mL) solution of benzyl alcohol (0.93 mL, 9 mmol), and the mixture was stirred at room temperature for 30 minutes. Thereafter, 5-fluoro-N-methyl-2-nitroaniline (510 mg, 3 mmol) was added thereto, and the mixture was stirred at room temperature for 3 hours. Water was added to the reaction solution, and precipitated crystals were collected by filtration. The resulting crystals were washed with water, and dried at 50° C., thereby obtaining 710 mg of orange, powdery 5-benzyloxy-N-methyl-2-nitroaniline (yield: 92%).

Example 5

An aqueous solution of 40% methyl amine (8.2 mL, 94.2 mmol) was added dropwise to a toluene solution (50 mL) of 2,4-difluoronitrobenzene (5.0 g, 31.4 mmol) under ice cooling, and the mixture was stirred at 35-40° C. for 2 hours. Water was added to the reaction solution, and toluene extraction was performed, followed by washing with water. Benzyl alcohol (6.5 mL, 62.8 mmol), tetrabutyl ammonium bromide (1.0 g, 3.1 mmol) and potassium carbonate (5.2 g, 37.6 mmol) were added to the resulting organic layer, and the mixture was heated under reflux for 4 hours. After the reaction solution was cooled, water (25 mL) was added, and the mixture was stirred at 70° C. for 1 hour. The mixture was stirred under ice cooling for 30 minutes, and precipitated crystals were collected by filtration. The resulting crystals were washed with water and dried at 50° C., thereby obtaining 7.8 g of orange, powdery 5-benzyloxy-N-methyl-2-nitroaniline (yield: 96%).

Example 6

An aqueous solution of 40% methyl amine (82 mL, 0.94 mol) was added dropwise to a toluene solution (500 mL) of 2,4-difluoronitrobenzene (50.0 g, 0.31 mol) under ice cooling, and the mixture was stirred for 2 hours at 35 to 40° C. Water was added to the reaction solution, and toluene extraction was performed, followed by washing with water. The resulting organic layer was concentrated under reduced pressure until reduced to about half. Benzyl alcohol (65 mL, 0.63 mol), tetrabutyl ammonium hydrogen sulfate (10.7 g, 31.5 mmol), potassium carbonate (65.2 g, 0.47 mol) and water (5 mL) were added to the resulting solution, and the resulting mixture was heated under reflux for 4 hours. After the reaction solution was cooled, water (250 mL) was added thereto, and the mixture was stirred at 70° C. for 1 hour. The mixture was stirred under ice cooling for 30 minutes, and then precipitated crystals were collected by filtration. After the resulting crystals were washed with water, methanol (500 mL) was added. The mixture was heated under reflux for 30 minutes, and then stirred at 10° C. or less for 1 hour. Precipitated crystals were collected by filtration, and then washed with methanol (100 mL). The resulting crystals were dried at 50° C., thereby obtaining 76.9 g of an orange, powdery 5-benzyloxy-N-methyl-2-nitroaniline (yield: 95%).

Example 7

Synthesis of N-(5-benzyloxy-2-nitrophenyl)-N-methylmaronamidic acid ethyl ester

A toluene solution (20 mL) of ethyl malonyl chloride (30.7 mL, 0.24 mol) was added dropwise to a toluene (230 mL) suspension of 5-benzyloxy-N-methyl-2-nitroaniline (51.6 g, 0.20 mol) at 50° C., and the mixture was stirred at 80° C. for 3 hours. The reaction solution was then cooled, and the solvent was distilled off under reduced pressure. Ethanol (100 mL) was added to the resulting residue, and the mixture was again distilled off under reduced pressure. Ethanol (100 mL) was added to the residue, and the residue was dispersed in and washed with the ethanol. Thereafter, precipitated crystals were collected by filtration. The resulting crystals were dried at 50° C., thereby obtaining 71.0 g of a light-yellow, powdery target compound (yield: 95%).

$^1$H-NMR (CDCl$_3$) δppm: 1.23 (2.52H, t, J=7.1 Hz), 1.32 (0.48H, t, J=7.1 Hz), 3.14 (1.68H, d, J=3.7 Hz), 3.24 (2.52H, s), 3.39 (0.48H, s), 3.5-3.7 (0.32H, br), 4.0-4.2 (1.68H, m), 4.24 (0.32H, q, J=7.1 Hz), 5.13 (0.32H, s), 5.17 (1.68H, s), 6.9-7.2 (2H, m), 7.3-7.5 (5H, m), 8.11 (0.16H, d, J=9.2 Hz), 8.14 (0.84H, d, J=9.2 Hz)

Example 8

Synthesis of 8-benzyloxy-1-methyl-1,5-dihydrobenzo[b][1,4]diazepine-2,4-dione

10% palladium carbon (4.00 g, water content: 52.1%) and diphenyl sulfide (0.18 mL, 1.08 mmol) were added to a methanol (400 mL) suspension of N-(5-benzyloxy-2-nitrophenyl)-N-methylmaronamidic acid ethyl ester (20.0 g, 53.7 mmol), and catalytic hydrogenation reaction was performed at 20° C. or less. The reaction solution was filtered, and the solvent was distilled off under reduced pressure at 25° C. or less. Toluene (50 mL) was added to the residue, and then the solvent was again distilled off under reduced pressure at 25° C. or less. Toluene (100 mL) was added to the residue, and then sodium t-butoxide (1.03 g, 10.7 mmol) was added thereto at room temperature, and the mixture was stirred overnight. Water (40 mL) was added to the reaction solution, and the mixture was stirred for 1 hour. Precipitated crystals were collected by filtration, and washed with toluene. The resulting crystals were dried at 60° C., thereby obtaining 12.4 g of a white, powdery target compound (yield: 78%).

$^1$H-NMR (CDCl$_3$) δppm: 3.35 (2H, s), 3.38 (3H, s), 5.09 (2H, s), 6.8-6.9 (2H, m), 7.09 (1H, d, J=9.6 Hz), 7.3-7.5 (5H, m), 9.22 (1H, brs)

Example 9

Synthesis of 7-benzyloxy-1-ethyl-5-methyl-1,5-dihydrobenzo[b][1,4]diazepine-2,4-dione 8-benzyloxy-1-methyl-1,5-dihydrobenzo[b][1,4]diazepine-2,4-dione (33.4 g, 113 mmol), tetrabutyl ammonium bromide (7.28 g, 22.6 mmol) and an aqueous solution of 25% sodium hydroxide (20.8 g, 130 mmol) were added to the mixture of toluene (167 mL) and water (150 mL). Ethyl iodide (10.4 mL, 130 mmol) was added thereto, and the reaction was performed at 80° C. for 4 hours. The reaction solution was cooled, and ethyl acetate (334 mL) extraction was performed. The resulting organic layer was washed with water, and the solvent was distilled off under reduced pressure. Ethyl acetate (70 mL) was added to the resulting residue, and the mixture was heated and dissolved. Thereafter, hexane (35 mL) was added thereto, and heating was performed again. The mixture was stirred at 40-50° C. for 30 minutes, and stirred under ice cooling for 1 hour to collect precipitated crystals by filtration. The resulting crystals were washed with ethyl acetate-hexane (1:1; 50 mL), and dried at 60° C., thereby obtaining 39.6 g of a light-yellow, powdery target compound (containing ammonium salt).

$^1$H-NMR (CDCl$_3$) δppm: 1.12 (3H, t, J=7.1 Hz), 3.2-3.4 (2H, m), 3.36 (3H, s), 3.5-3.7 (1H, m), 4.1-4.3 (1H, m), 5.09 (2H, s), 6.86 (1H, d, J=2.8 Hz), 6.91 (1H, dd, J=2.8 Hz, 8.9 Hz), 7.25 (1H, d, J=8.9 Hz), 7.3-7.5 (5H, m)

Example 10

Sodium t-butoxide (330 mg, 3.43 mmol) was added to a N,N-dimethylformamide (5 mL) solution of 8-benzyloxy-1-methyl-1,5-dihydrobenzo[b][1,4]diazepine-2,4-dione (1.01 g, 3.4 mmol) under ice cooling, and the mixture was stirred under ice cooling for 30 minutes. Thereafter, diethyl sulfate (0.51 mL, 3.69 mmol) was added, and the mixture was stirred for 6 hours under ice cooling. Water was added to the reaction solution, and ethyl acetate (20 mL) extraction was performed. The resulting organic layer was washed with water, and the solvent was distilled off under reduced pressure. The resulting residue was recrystallized from 50% ethanol (9 mL). Precipitated crystals were collected by filtration, washed with 50% ethanol, and dried at 60° C., thereby obtaining 760 mg of light-yellow, powdery 7-benzyloxy-1-ethyl-5-methyl-1,5-dihydrobenzo[b][1,4]diazepine-2,4-dione (yield: 69%).

Example 11

Synthesis of 7-benzyloxy-1-ethyl-3,3,5-trimethyl-1,5-dihydrobenzo[b][1,4]diazepine-2,4-dione Under ice cooling, sodium hydride (60% in oil) (5.2 g, 130 mmol) was added to an N,N-dimethylformamide (300 mL) suspension of 1-ethyl-7-benzyloxy-5-methyl-1,5-dihydrobenzo[b][1,4]diazepine-2,4-dione (35.2 g, 109 mmol), and the mixture was stirred at 0° C. for 30 minutes. Thereafter, an N,N-dimethylformamide (10 mL) solution of methyl iodide (8.1 mL, 130 mmol) was added dropwise thereto. The reaction solution was stirred at the same temperature for 1 hour, and then stirred at room temperature for 1 hour. The reaction solution was cooled to 0° C., and sodium hydride (60% in oil) (7.8 g, 195 mmol) was added thereto. After the mixture was stirred at 0° C. for 30 minutes, an N,N-dimethylformamide (10 mL) solution of methyl iodide (12.2 mL, 196 mmol) was added dropwise. The reaction solution was stirred at the same temperature for 2 hours, and then stirred at room temperature overnight. Ice water was added to the reaction solution, and precipitated crystals were collected by filtration. The resulting crystals were washed with water, and added to methanol (210 mL). The mixture was stirred while heating, and allowed to stand overnight at room temperature. Precipitated crystals were washed with 50% methanol, and dried at 60° C., thereby obtaining 38.3 g of a white, powdery target compound (yield: quantitative amount).

$^1$H-NMR (CDCl$_3$) δppm: 0.86 (3H, s), 1.15 (3H, t, J=7.1 Hz), 1.53 (3H, s), 3.37 (3H, s), 3.6-3.8 (1H, m), 4.1-4.3 (1H, m), 5.09 (2H, s), 6.80 (1H, d, J=2.8 Hz), 6.90 (1H, dd, J=2.8 Hz, 9.0 Hz), 7.22 (1H, d, J=9.0 Hz), 7.3-7.5 (5H, m)

Example 12

Synthesis of 7-benzyloxy-1-ethyl-3,5-dimethyl-1,5-dihydrobenzo[b][1,4]diazepine-2,4-dione After sodium t-butoxide (1.53 g, 15.9 mmol) was added to a dimethoxyethane (20 mL) suspension of 1-ethyl-7-benzyloxy-5-methyl-1,5-dihydrobenzo[b][1,4]diazepine-2,4-dione (4.31 g, 13.3 mmol) under ice cooling, the mixture was stirred at room temperature for 30 minutes. Thereafter, dimethoxyethane (2 mL) of methyl p-toluenesulfonate (2.6 mL, 17.2 mmol) was added thereto under ice cooling, and the mixture was stirred under ice cooling for 2 hours. The reaction solution was poured into ice water, and ethyl acetate (50 mL) extraction was performed. The resulting organic layer was washed with water, and the solvent was distilled off. The resulting residue was subjected to silica gel column chromatography (elution solvent: 2:3=ethyl acetate:n-hexane). The solvent was distilled off, thereby obtaining 3.78 g of a colorless liquid target compound (yield: 84%).

$^1$H-NMR (CDCl$_3$) δppm: 1.10 (3H, t, J=7.1 Hz), 1.36 (3H, d, J=6.6 Hz), 3.2-3.3 (1H, m), 3.39 (3H, s), 3.5-3.7 (1H, m), 4.2-4.4 (1H, m), 5.11 (2H, s), 6.87 (1H, d, J=2.7 Hz), 6.93 (1H, dd, J=2.7 Hz, 8.9 Hz), 7.28 (1H, d, J=8.9 Hz), 7.3-7.5 (5H, m)

Example 13

Synthesis of 7-benzyloxy-3-butyl-1-ethyl-3,5-dimethyl-1,5-dihydrobenzo[b][1,4]diazepine-2,4-dione Under ice cooling, sodium hydride (60% in oil) (129 mg, 3.23 mmol) was added to a N,N-dimethylformamide (5 mL)

solution of 7-benzyloxy-1-ethyl-3,5-dimethyl-1,5-dihydrobenzo[b][1,4]diazepine-2,4-dione (500 mg, 1.48 mmol), and the mixture was stirred at 0° C. for 30 minutes. Thereafter, butyl iodide (0.336 mL, 2.95 mmol) was added. The reaction solution was stirred at 0° C. for 30 minutes, and then stirred at room temperature for 2 hours. The reaction solution was poured into ice water, and ethyl acetate (20 mL) extraction was performed. The resulting organic layer was washed with water, and the solvent was distilled off. The resulting residue was subjected to silica gel column chromatography (elution solvent: 1:2=ethyl acetate:n-hexane). The solvent was distilled off, thereby obtaining 520 mg of a colorless, liquid target compound (yield: 89%).

$^1$H-NMR (CDCl$_3$) δppm: 0.61 (3H, t, J=6.9 Hz), 0.8-1.1 (6H, m), 1.17 (3H, t, J=7.2 Hz), 1.52 (3H, s), 3.36 (3H, s), 3.6-3.8 (1H, m), 4.0-4.2 (1H, m), 5.10 (2H, s), 6.79 (1H, d, J=2.7 Hz), 6.88 (1H, dd, J=2.7 Hz, 9.0 Hz), 7.20 (1H, d, J=9.0 Hz), 7.3-7.5 (5H, m)

Example 14

Synthesis of 5-benzyloxy-N$^1$-methylbenzene-1,2-diamine hydrochloride

5% platinum carbon (2.15 g, water content: 53.1%) was added to a toluene (300 mL) suspension of 5-benzyloxy-N-methyl-2-nitroaniline (20 g, 77.4 mmol), and catalytic hydrogenation reaction was performed at 4 atm. The reaction solution was filtered to remove a catalyst. The catalyst was washed with 2-propanol (40 mL), and the washing liquid was added to the precedent filtrate. Under ice cooling, concentrated hydrochloric acid (6.6 mL, 77.4 mmol) was added to the mixture, and the mixture was stirred under the same temperature for 30 minutes. The resulting precipitated crystals were collected by filtration, then washed with 2-propanol (60 mL), and dried at 50° C., thereby obtaining 18.6 g of a light-pink, crystal target compound (yield: 91%)

$^1$H-NMR (DMSO-d$_6$) δppm: 2.72 (3H, s), 5.09 (2H, s), 6.2-6.4 (2H, m), 7.13 (1H, d, J=8.8 Hz), 7.3-7.5 (5H, m), 9.2-10.2 (4H, br)

Example 15

Synthesis of 5-benzyloxy-N$^1$-methylbenzene-1,2-diamine ½ sulfate

5% platinum carbon (0.50 g, (DRY)) was added to a 2-propanol (170 mL) suspension of 5-benzyloxy-N-methyl-2-nitroaniline (10.00 g, 38.7 mmol), and catalytic hydrogenation reaction was performed at ordinary pressure. The reaction solution was filtered to remove a catalyst. The catalyst was washed with 2-propanol (20 mL), and the washing liquid was added to the precedent filtrate. Under ice cooling, 97% sulfuric acid (1.06 mL, 19.3 mmol) was added to the mixture, and then the mixture was stirred under the same temperature for 30 minutes. The resulting precipitated crystals were collected by filtration, then washed with 2-propanol (40 mL), and dried at 40° C., thereby obtaining 9.07 g of a light-purple, crystal target compound (yield: 94.7%).

$^1$H-NMR (DMSO-d$_6$) δppm: 2.72 (3H, s), 2.8-4.2 (4H, br), 5.09 (2H, s), 6.2-6.4 (2H, m), 6.84 (1H, d, J=8.9 Hz), 7.3-7.5 (5H, m)

Example 16

Synthesis of 8-benzyloxy-1,3,3-trimethyl-1,5-dihydrobenzo[b][1,4]diazepine-2,4-dione Under ice cooling, dimethylmalonic acid dichloride (9.9 mL, 74.9 mmol) was added dropwise to a N,N-dimethyl acetamide (90 mL) solution of 5-benzyloxy-N$^1$-methylbenzene-1,2-diamine hydrochloride (18.0 g, 68.0 mmol). The mixture was stirred at the same temperature for 2.5 hours, and water (90 mL) was added thereto. The reaction solution was stirred at 10° C. or less for 30 minutes, and precipitated crystals were collected by filtration. The resulting crystals were washed with water, then added to methanol (180 mL), and heated under reflux. The mixture was cooled and stirred at 10° C. or less for 30 minutes, and precipitated crystals were collected by filtration. The resulting crystals were washed with methanol (36 mL), and dried at 60° C., thereby obtaining 18.3 g of a white, powdery target compound (yield: 83%).

$^1$H-NMR (CDCl$_3$) δppm: 0.8-1.7 (6H, br), 3.41 (3H, s), 5.08 (2H, s), 6.8-6.9 (2H, m), 6.97 (1H, d, J=9.2 Hz), 7.3-7.5 (5H, m), 8.55 (1H, brs)

Example 17

Synthesis of 8-benzyloxy-1,3,3-trimethyl-1,5-dihydrobenzo[b][1,4]diazepine-2,4-dione Under ice cooling, a N,N-dimethylacetamide (3 mL) solution of dimethylmalonic acid dichloride (0.68 g, 4.0 mmol) was added dropwise to a N,N-dimethyl acetamide (5 mL) suspension of 5-benzyloxy-N$^1$-methylbenzene-1,2-diamine ½ sulfate (1.11 g, 4.0 mmol). After the reaction solution was stirred at the same temperature for 4 hours, water (8 mL) was added. The mixture was stirred at 10° C. or less for 30 minutes, and precipitated crystals were collected by filtration. The resulting crystals were washed with water, and dried at 60° C., thereby obtaining 0.75 g of a slightly pink, powdery target compound (yield: 57.8%).

Example 18

Synthesis of 8-benzyloxy-3,3-diethyl-1-methyl-1,5-dihydrobenzo[b][1,4]diazepine-2,4-dione A target compound was synthesized in the same manner as in Example 16, using a suitable starting material.

$^1$H-NMR (CDCl$_3$) δppm: 0.84 (6H, t, J=6.9 Hz), 1.5-1.9 (4H, br), 3.40 (3H, s), 5.08 (2H, s), 6.7-6.9 (2H, m), 6.97 (1H, d, J=8.4 Hz), 7.3-7.5 (5H, m), 8.80 (1H, brs)

Example 19

Synthesis of 7-benzyloxy-1-ethyl-3,3,5-trimethyl-1,5-dihydrobenzo[b][1,4]diazepine-2,4-dione Under ice cooling, sodium t-butoxide (1.96 g, 20.4 mmol) was added to a N,N-dimethylacetamide (30 mL) solution of 8-benzyloxy-1,3,3-trimethyl-1,5-dihydrobenzo[b][1,4]diazepine-2,4-dione (6.0 g, 18.5 mmol), and the mixture was stirred for 30 minutes. 1.63 mL (20.4 mmol) of ethyl iodide was added dropwise. The reaction solution was stirred at 10-20° C. for 4 hours. Water (42 mL) was added to the reaction solution, and the mixture was stirred at 10° C. or less for 30 minutes. Thereafter, precipitated crystals were collected by filtration, and the crystals were added to methanol (60 mL). The resultant was heated under reflux, and stirred at 10° C. or less for 30 minutes. Crystals were collected by filtration, then washed with methanol, and dried at 60° C., thereby obtaining 5.90 g of a white, powdery target compound (yield: 91%).

$^1$H-NMR (CDCl$_3$) δppm: 0.86 (3H, s), 1.15 (3H, t, J=7.1 Hz), 1.53 (3H, s), 3.37 (3H, s), 3.6-3.8 (1H, m), 4.1-4.3 (1H, m), 5.09 (2H, s), 6.80 (1H, d, J=2.8 Hz), 6.90 (1H, dd, J=2.8 Hz, 9.0 Hz), 7.22 (1H, d, J=9.0 Hz), 7.3-7.5 (5H, m)

Example 20

Synthesis of 7-benzyloxy-1-butyl-3,3,5-trimethyl-1,5-dihydrobenzo[b][1,4]diazepine-2,4-dione The target compound was synthesized in the same manner as in Example 19, using a suitable starting material.
$^1$H-NMR (CDCl$_3$) δppm: 0.83 (3H, t, J=7.5 Hz), 0.85 (3H, s), 1.1-1.3 (2H, m), 1.4-1.6 (2H, m), 1.52 (3H, s), 3.37 (3H, s), 3.5-3.7 (1H, m), 4.2-4.4 (1H, m), 5.08 (2H, s), 6.80 (1H, d, J=3.0 Hz), 6.90 (1H, dd, J=3.0 Hz, 9.0 Hz), 7.20 (1H, d, J=9.0 Hz), 7.3-7.5 (5H, m)

Example 21

Synthesis of 7-benzyloxy-1-isopentyl-3,3,5-trimethyl-1,5-dihydrobenzo[b][1,4]diazepine-2,4-dione The target compound was synthesized in the same manner as in Example 19, using a suitable starting material.
$^1$H-NMR (CDCl$_3$) δppm: 0.82 (3H, d, J=6.3 Hz), 0.85 (3H, s), 0.87 (3H, d, J=6.3 Hz), 1.3-1.5 (3H, m), 1.52 (3H, s), 3.36 (3H, s), 3.5-3.7 (1H, m), 4.2-4.4 (1H, m), 5.08 (2H, s), 6.80 (1H, d, J=2.7 Hz), 6.90 (1H, dd, J=2.7 Hz, 9.0 Hz), 7.21 (1H, d, J=9.0 Hz), 7.3-7.5 (5H, m)

Example 22

Synthesis of 1-ethyl-7-hydroxy-3,3,5-trimethyl-1,5-dihydrobenzo[b][1,4]diazepine-2,4-dione 10% palladium carbon (1.66 g, water content: 54.8%) was added to an ethanol (150 mL) solution of 1-ethyl-7-benzyloxy-3,3,5-trimethyl-1,5-dihydrobenzo[b][1,4]diazepine-2,4-dione (15.0 g, 42.6 mmol), and catalytic hydrogenation reaction was performed at 40-50° C., at 3 atm. The reaction solution was filtered to remove a catalyst, and ethanol was distilled off. Methanol (105 mL) and water (105 mL) were added to the resulting residue, and the mixture was heated while stirring. After the dissolution was confirmed, stirring under ice cooling was conducted for 1 hour, and precipitated crystals were collected by filtration. The resulting crystals were washed with 50% methanol (30 mL), and dried at 60° C., thereby obtaining 10.7 g of a white, powdery target compound (yield: 96%).
$^1$H-NMR (CDCl$_3$) δppm: 0.90 (3H, s), 1.16 (3H, t, J=7.1 Hz), 1.55 (3H, s), 3.41 (3H, s), 3.6-3.8 (1H, m), 4.1-4.3 (1H, m), 6.80 (1H, d, J=2.7 Hz), 6.85 (1H, dd, J=2.7 Hz, 8.8 Hz), 7.17 (1H, d, J=8.8 Hz), 7.49 (1H, brs)

Example 23

20% palladium hydroxide carbon (4.00 g) was added to a methanol (400 mL) solution of 1-ethyl-7-benzyloxy-3,3,5-trimethyl-1,5-dihydrobenzo[b][1,4]diazepine-2,4-dione (39.8 g, 113 mmol), and catalytic hydrogenation reaction was performed at room temperature at ordinary pressure. The reaction solution was filtered to remove a catalyst, and methanol was distilled off. Ethanol (120 mL) was added to the resulting residue, and the mixture was heated while stirring. After the dissolution was confirmed, water (40 mL) was added, and the mixture was heated again. After the temperature was cooled to near room temperature, stirring was performed under ice cooling for 1 hour. Precipitated crystals were then collected by filtration. The resulting crystals were washed with 50% ethanol (40 mL), and dried at 60° C., thereby obtaining 24.3 g of white, powdery 1-ethyl-7-hydroxy-3,3,5-trimethyl-1,5-dihydrobenzo[b][1,4]diazepine-2,4-dione (yield: 82%).

Example 24

Synthesis of 1-butyl-7-hydroxy-3,3,5-trimethyl-1,5-dihydrobenzo[b][1,4]-diazepine-2,4-dione The target compound was synthesized in the same manner as in Example 22, using a suitable starting material.
$^1$H-NMR (CDCl$_3$) δppm: 0.82 (3H, t, J=7.2 Hz), 0.88 (3H, s), 1.1-1.3 (2H, m), 1.3-1.6 (2H, m), 1.54 (3H, s), 3.40 (3H, s), 3.5-3.7 (1H, m), 4.2-4.4 (1H, m), 6.79 (1H, d, J=2.7 Hz), 6.84 (1H, dd, J=2.7 Hz, 8.7 Hz), 7.15 (1H, d, J=8.7 Hz), 7.29 (1H, brs).

Example 25

Synthesis of 7-hydroxy-1-isopentyl-3,3,5-trimethyl-1,5-dihydrobenzo[b][1,4]diazepine-2,4-dione The target compound was synthesized in the same manner as in Example 22, using a suitable starting material.
$^1$H-NMR (CDCl$_3$) δppm: 0.82 (3H, d, J=6.3 Hz), 0.86 (3H, d, J=6.0 Hz), 0.88 (3H, s), 1.3-1.5 (3H, m), 1.54 (3H, s), 3.39 (3H, s), 3.5-3.7 (1H, m), 4.2-4.4 (1H, m), 6.76 (1H, d, J=2.7 Hz), 6.82 (1H, dd, J=2.7 Hz, 9.0 Hz), 6.8-7.0 (1H, br), 7.16 (1H, d, J=9.0 Hz)

Example 26

Synthesis of 3,3-diethyl-8-hydroxy-1-methyl-1,5-dihydrobenzo[b][1,4]diazepine-2,4-dione The target compound was synthesized in the same manner as in Example 22, using a suitable starting material.
$^1$H-NMR (DMSO-d$_6$) δppm: 0.72 (6H, brs), 1.3-1.9 (4H, br), 3.30 (3H, s), 6.64 (1H, dd, J=2.4 Hz, 8.7 Hz), 6.72 (1H, d, J=2.4 Hz), 6.92 (1H, d, J=8.7 Hz), 9.3-9.8 (1H, br), 10.12 (1H, brs)

Example 27

Synthesis of 3-butyl-1-ethyl-7-hydroxy-3,5-dimethyl-1,5-dihydrobenzo[b][1,4]diazepine-2,4-dione The target compound was synthesized in the same manner as in Example 22, using a suitable starting material.
$^1$H-NMR (CDCl$_3$) δppm: 0.63 (3H, t, J=7.2 Hz), 0.8-1.2 (6H, m), 1.18 (3H, t, J=7.2 Hz), 1.56 (3H, s), 3.40 (3H, s), 3.6-3.8 (1H, m), 4.0-4.2 (1H, m), 6.79 (1H, d, J=2.7 Hz), 6.84 (1H, dd, J=2.7 Hz, 9.0 Hz), 7.17 (1H, d, J=9.0 Hz), 7.50 (1H, brs)

Example 28

Synthesis of 1-ethyl-7-hydroxy-5-methyl-1,5-dihydrobenzo[b][1,4]diazepine-2,4-dione The target compound was synthesized in the same manner as in Example 23, using a suitable starting material.
$^1$H-NMR (DMSO-d$_6$) δppm: 0.96 (3H, t, J=7.2 Hz), 2.96 (1H, d, J=12.3 Hz), 3.25 (3H, s), 3.39 (1H, d, J=12.3 Hz), 3.5-3.7 (1H, m), 3.9-4.2 (1H, m), 6.75 (1H, dd, J=2.7 Hz, 8.7 Hz), 6.80 (1H, d, J=2.7 Hz), 7.33 (1H, d, J=8.7 Hz), 9.5-10.5 (1H, br)

Example 29

Synthesis of 5-benzyloxy-N-ethyl-2-nitroaniline

An aqueous solution of 70% ethyl amine (25 mL, 0.315 mol) was added dropwise to a toluene solution (167 mL) of 2,4-difluoronitrobenzene (16.7 g, 0.105 mol) under ice cooling, and the mixture was stirred at 35-40° C. for 2 hours. Water was added to the reaction solution, and toluene extraction was performed, followed by washing with water. The resulting organic layer was concentrated under reduced pressure until reduced to about half (the concentrated solution including a crude product of 5-fluoro-N-ethyl-2-nitroaniline). Benzyl alcohol (21.7 mL, 0.21 mol), tetrabutyl ammonium hydrogen sulfate (3.56 g, 0.01 mmol), potassium carbonate (21.76 g, 0.157 mol), and water (1.7 mL) were added to the resulting solution, and the mixture was heated under reflux for 3 hours. The reaction solution was cooled, and water (84 mL) was added thereto. Thereafter, the mixture was stirred at 70° C. for 1 hour, and stirred under ice cooling for 30 minutes. Next, precipitated crystals were collected by filtration, and the resulting crystals were washed with water, and dried at 50° C., thereby obtaining 17.7 g of a yellow, powdery target compound (yield: 62%).
$^1$H-NMR (CDCl$_3$) δppm: 1.34 (3H, t, J=7.3 Hz), 3.28 (2H, q, J=7.3 Hz), 5.12 (2H, s), 6.22 (1H, d, J=2.7 Hz), 6.30 (1H, dd, J=2.7 Hz, 9.2 Hz), 7.2-7.5 (5H, m), 8.14 (1H, d, J=9.2 Hz), 8.1-8.3 (1H, br)

Example 30

Synthesis of 5-benzyloxy-N-isobutyl-2-nitroaniline

Isobutylamine (25 mL, 121 mmol) was added dropwise to a toluene solution (40 mL) of 2,4-difluoronitrobenzene (8.0 g, 50.3 mmol) under ice cooling, and the mixture was stirred at 35-40° C. for 2 hours. Water was added to the reaction solution, and toluene extraction was performed, followed by washing with water. The resulting organic layer was concentrated under reduced pressure until reduced to about half (the concentrated solution including a crude product of 5-fluoro-N-isobutyl-2-nitroaniline). Benzyl alcohol (10.4 mL, 100 mmol), tetrabutyl ammonium hydrogen sulfate (1.71 g, 5.0 mmol), potassium carbonate (10.42 g, 75.4 mmol), and water (0.8 mL) were added to the resulting solution, and the mixture was heated under reflux for 3 hours. After the reaction solution was cooled, water (84 mL) was added thereto, followed by toluene extraction. After the resulting organic layer was washed with water, the solvent was distilled off, and cyclopentyl ether was added to the resulting residue. The mixture was stirred for 1 hour. Precipitated crystals were collected by filtration, and the resulting crystals were dried at 50° C., thereby obtaining 12.2 g of a yellow, powdery target compound (yield: 81%).
$^1$H-NMR (CDCl$_3$) δppm: 1.03 (6H, d, J=6.5 Hz), 1.8-2.1 (1H, m), 3.0-3.1 (2H, m), 5.12 (2H, s), 6.21 (1H, d, J=2.7 Hz), 6.29 (1H, dd, J=2.7 Hz, 9.5 Hz), 7.2-7.5 (5H, m), 8.15 (1H, d, J=9.5 Hz), 8.38 (1H, brs)

Example 31

Synthesis of 5-benzyloxy-N$^1$-ethylbenzene-1,2-diamine hydrochloride

The target compound was synthesized in the same manner as in Example 14, using a suitable starting material.
$^1$H-NMR (DMSO-d$_6$) δppm: 1.21 (3H, t, J=7.3 Hz), 3.06 (2H, q, J=7.3 Hz), 5.08 (2H, s), 6.3-6.4 (2H, m), 7.13 (1H, d, J=9.2 Hz), 7.2-7.5 (5H, m), 9.2-10.3 (4H, br)

Example 32

Synthesis of 5-benzyloxy-N$^1$-isobutylbenzene-1,2-diamine hydrochloride

The target compound was synthesized in the same manner as in Example 14, using a suitable starting material.
$^1$H-NMR (DMSO-d$_6$) δppm: 0.97 (6H, d, J=6.5 Hz), 1.7-2.0 (1H, m), 2.84 (2H, d, J=7.0 Hz), 5.08 (2H, s), 6.2-6.4 (2H, m), 7.15 (1H, d, J=8.1 Hz), 7.3-7.5 (5H, m), 9.7-10.3 (4H, br)

Example 33

Synthesis of 8-benzyloxy-1-ethyl-3,3-dimethyl-1,5-dihydrobenzo[b][1,4]diazepine-2,4-dione The target compound was synthesized in the same manner as in Example 16, using a suitable starting material.
$^1$H-NMR (CDCl$_3$) δppm: 1.02 (3H, s), 1.19 (3H, t, J=7.3 Hz), 1.72 (3H, s), 3.7-4.2 (2H, m), 5.08 (2H, s), 6.8-6.9 (2H, m), 7.01 (1H, d, J=8.6 Hz), 7.3-7.6 (5H, m), 8.6-9.1 (1H, br)

Example 34

Synthesis of 8-benzyloxy-1-isobutyl-3,3-dimethyl-1,5-dihydrobenzo[b][1,4]diazepine-2,4-dione The target compound was synthesized in the same manner as in Example 16, using a suitable starting material.
$^1$H-NMR (CDCl$_3$) δppm: 0.71 (6H, d, J=6.5 Hz), 0.99 (3H, s), 1.52 (3H, s), 1.7-1.9 (1H, m), 3.2-3.5 (1H, m), 4.2-4.4 (1H, m), 5.08 (2H, d, J=4.6 Hz), 6.8-6.9 (2H, m), 6.99 (1H, d, J=10.0 Hz), 7.3-7.5 (5H, m), 8.55 (1H, brs)

Example 35

Synthesis of 7-benzyloxy-1,5-diethyl-3,3-dimethyl-1,5-dihydrobenzo[b][1,4]diazepine-2,4-dione The target compound was synthesized in the same manner as in Example 19, using a suitable starting material.
$^1$H-NMR (CDCl$_3$) δppm: 0.84 (3H, s), 1.0-1.2 (6H, m), 1.48 (3H, s), 3.5-3.7 (2H, m), 4.2-4.4 (2H, m), 5.09 (2H, s), 6.8-7.0 (2H, m), 7.1-7.3 (1H, m), 7.3-7.5 (5H, m)

Example 36

Synthesis of 7-benzyloxy-1-ethyl-5-isobutyl-3,3-dimethyl-1,5-dihydrobenzo[b][1,4]diazepine-2,4-dione The target compound was synthesized in the same manner as in Example 19, using a suitable starting material.
$^1$H-NMR (CDCl$_3$) δppm: 0.73 (6H, dd, J=5.7 Hz, 6.5 Hz), 0.83 (3H, s), 1.22 (3H, t, J=7.3 Hz), 1.51 (3H, s), 1.6-1.8 (1H, m), 3.1-3.3 (1H, m), 3.7-3.9 (1H, m), 4.0-4.2 (1H, m), 4.2-4.4 (1H, m), 5.0-5.2 (2H, m), 6.82 (1H, d, J=2.7 Hz), 6.91 (1H, dd, J=2.7 Hz, 8.9 Hz), 7.22 (1H, d, J=8.9 Hz), 7.3-7.5 (5H, m)

Example 37

Synthesis of 1,5-diethyl-7-hydroxy-3,3-dimethyl-1,5-dihydrobenzo[b][1,4]diazepine-2,4-dione The target compound was synthesized in the same manner as in Example 23, using a suitable starting material.

$^1$H-NMR (CDCl$_3$) δppm: 0.88 (3H, s), 1.11 (3H, t, J=7.3 Hz), 1.15 (3H, t, J=7.0 Hz), 1.54 (3H, s), 3.5-3.8 (2H, m), 4.2-4.5 (2H, m), 6.8-7.0 (2H, m), 7.17 (1H, d, J=9.5 Hz), 7.2-7.7 (1H, br)

Example 38

Synthesis of 1-ethyl-7-hydroxy-5-isobutyl-3,3-dimethyl-1,5-dihydrobenzo[b][1,4]diazepine-2,4-dione The target compound was synthesized in the same manner as in Example 23, using a suitable starting material.

$^1$H-NMR (CDCl$_3$) δppm: 0.78 (6H, dd, J=6.8 Hz, 13.5 Hz), 0.87 (3H, s), 1.24 (3H, t, J=7.3 Hz), 1.54 (3H, s), 1.7-2.0 (1H, m), 3.2-3.4 (1H, m), 3.7-3.9 (1H, m), 4.0-4.3 (1H, m), 4.3-4.5 (1H, m), 6.8 (2H, m), 6.9-7.2 (1H, br), 7.18 (1H, d, J=9.5 Hz)

Example 39

Synthesis of 3-fluoro-N-methyl-2-nitroaniline

A methanol solution of 40% methyl amine (12.2 mL, 119 mmol) was added dropwise to a methanol solution (39.5 mL) of 2,6-difluoronitrobenzene (7.90 g, 49.7 mmol) under ice cooling, and the mixture was stirred at the same temperature for 0.5 hours, and then stirred at room temperature for 3 hours. The reaction solution was poured into ice water, and precipitated crystals were collected by filtration, and washed with water. The resulting crystals were dried at 50° C., thereby obtaining 7.84 g of a red, powdery target compound (yield: 93%).

$^1$H-NMR (CDCl$_3$) δppm: 2.98 (3H, d, J=5.1 Hz), 6.43 (1H, dd, J=11.6 Hz, 8.9 Hz), 6.57 (1H, d, 8.9 Hz), 7.2-7.4 (2H, m)

Example 40

Synthesis of 3-benzyloxy-N-methyl-2-nitroaniline

Benzyl alcohol (9.54 mL, 92.2 mmol), tetrabutyl ammonium bromide (1.49 g, 4.62 mmol), and potassium carbonate (7.64 g, 55.3 mmol) were added to a toluene solution (39 mL) of 3-fluoro-N-methyl-2-nitroaniline (7.84 g, 46.1 mmol), and the mixture was heated under reflux for 6 hours. The reaction solution was cooled, and water (39 mL) was added thereto, followed by toluene extraction. The resulting organic layer was washed with water, and the solvent was distilled off under reduced pressure, thereby obtaining 11.9 g of a red, powdery target compound (yield: 100%).

$^1$H-NMR (CDCl$_3$) δppm: 2.90 (3H, d, J=4.9 Hz), 5.15 (2H, s), 6.2-6.4 (2H, m), 7.0-7.5 (7H, m)

Example 41

Synthesis of 3-benzyloxy-N$^1$-methylbenzene-1,2-diamine hydrochloride 0.80 g of 5% platinum carbon (dry) was added to a toluene (80 mL) suspension of 3-benzyloxy-N-methyl-2-nitroaniline (7.19 g, 27.8 mmol), and catalytic hydrogenation reaction was performed under ordinary pressure. The reaction solution was filtered to remove a catalyst, and the catalyst was washed with toluene (10 mL). The washing liquid was added to the precedent filtrate. A 1N hydrochloric acid ethanol solution (28 mL, 28.0 mmol) was added to the mixture under ice cooling, and the mixture was stirred under the same temperature for 30 minutes. The solvent was distilled off under reduced pressure at 20° C. or less. Precipitated crystals were collected by filtration, washed with toluene (15 mL), and dried at 40° C., thereby obtaining 6.30 g of an orange, crystal target compound (yield: 85%).

$^1$H-NMR (DMSO-d$_6$) δppm: 2.80 (3H, s), 5.19 (2H, s), 5.4-6.6 (4H, br), 6.66 (1H, d, J=8.4 Hz), 6.74 (1H, d, J=8.1 Hz), 6.94 (1H, dd, J=8.1 Hz, 8.4 Hz), 7.3-7.6 (5H, m)

Example 42

Synthesis of 6-benzyloxy-1,3,3-trimethyl-1,5-dihydrobenzo[b][1,4]diazepine-2,4-dione The target compound was synthesized in the same manner as in Example 16, using a suitable starting material.

$^1$H-NMR (CDCl$_3$) δppm: 0.8-1.7 (6H, br), 3.45 (3H, s), 5.15 (2H, s), 6.83 (1H, d, J=8.1 Hz), 6.87 (1H, d, J=8.1 Hz), 7.13 (1H, dd, J=8.1 Hz, 8.1 Hz), 7.3-7.5 (5H, m), 7.89 (1H, brs)

Example 43

Synthesis of 6-benzyloxy-5-ethyl-1,3,3-trimethyl-1,5-dihydrobenzo[b][1,4]diazepine-2,4-dione 60% sodium hydride (0.37 g, 8.5 mmol) was added to a N,N-dimethylacetamide (12.5 mL) solution of 6-benzyloxy-1,3,3-trimethyl-1,5-dihydrobenzo[b][1,4]diazepine-2,4-dione (2.5 g, 7.7 mmol) under ice cooling, and the mixture was stirred for 30 minutes. Ethyl iodide (0.68 mL, 8.5 mmol) was added dropwise thereto, followed by stirring at 10-20° C. for 2 hours. Water (17.5 mL) was added to the reaction solution, and ethyl acetate (20 mL) was added, followed by ethyl acetate extraction. The resulting organic layer was washed with water, and the solvent was distilled off. An aqueous solution of 70% methanol was added to the resulting residue, and the mixture was heated under reflux for 1 hour, followed by stirring for 30 minutes under ice cooling. Crystals were collected by filtration, then washed with an aqueous solution of 70% methanol, and dried at 60° C., thereby obtaining 2.71 g of a white, powdery target compound (yield: 100%).

$^1$H-NMR (CDCl$_3$) δppm: 0.77 (3H, s), 0.91 (3H, t, J=7.3 Hz), 1.52 (3H, s), 3.40 (3H, s), 3.3-3.7 (1H, m), 4.2-4.4 (1H, m), 5.15 (2H, s), 6.8-7.0 (2H, m), 7.26 (1H, dd, J=8.1 Hz, 8.4 Hz), 7.3-7.5 (5H, m)

Example 44

Synthesis of 5-ethyl-6-hydroxy-1,3,3-trimethyl-1,5-dihydrobenzo[b][1,4]diazepine-2,4-dione The target compound was synthesized in the same manner as in Example 23, using a suitable starting material.

$^1$H-NMR (DMSO-d$_6$) δppm: 0.70 (3H, s), 0.81 (3H, t, J=7.3 Hz), 1.31 (3H, s), 3.29 (3H, s), 3.4-3.6 (2H, m), 4.0-4.2 (1H, m), 6.84 (1H, d, J=8.1 Hz), 6.90 (1H, d, J=8.4 Hz), 7.21 (1H, dd, J=8.1 Hz, 8.4 Hz), 10.30 (1H, brs)

The invention claimed is:

1. A process for producing a compound represented by formula (1),

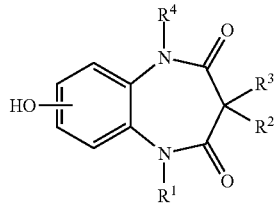
(1)

wherein each of $R^1$, $R^2$, $R^3$ and $R^4$, which may be the same or different, represents a hydrogen atom or a lower alkyl group, the process comprising deprotecting a protective group ($R^5$) of a compound represented by formula (2),

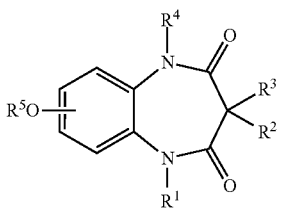
(2)

wherein $R^1$, $R^2$, $R^3$ and $R^4$ are as defined above, and $R^5$ is a benzyl group that may be substituted by a group selected from the group consisting of lower alkyl groups, halogen atoms, cyano groups, lower alkoxy groups, nitro groups, phenyl groups and acyl groups, by reducing the compound represented by formula (2) in the presence of a catalytic hydrogenation reducing agent in a hydrogen atmosphere at 1 to 20 atm at −20 to 150° C., wherein the catalytic hydrogenation reducing agent is at least one member selected from the group consisting of palladium black, palladium carbon, palladium hydroxide carbon, platinum carbon, platinum, platinum black, platinum oxide, copper chromite and Raney nickel.

2. The process according to claim 1 for producing a compound represented by formula (1A),

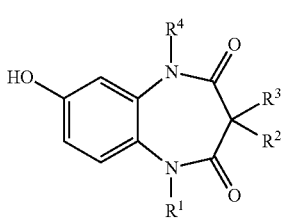
(1A)

wherein $R^1$, $R^2$, $R^3$ and $R^4$ are as defined above,
the process comprising deprotecting a protective group ($R^5$) of a compound represented by formula (2A),

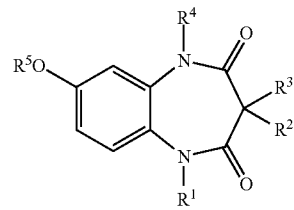
(2A)

wherein $R^1$, $R^2$, $R^3$, $R^4$ and $R^5$ are as defined above.

3. The process according to claim 1, wherein the amount of the catalytic hydrogenation reducing agent is 0.1 to 40 wt %, relative to the compound represented by formula (2).

4. A process for producing a compound represented by formula (2h),

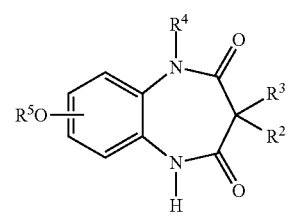
(2h)

wherein each of $R^2$, $R^3$ and $R^4$, which may be the same or different, represents a hydrogen atom or a lower alkyl group, and $R^5$ is a benzyl group that may be substituted by a group selected from the group consisting of lower alkyl groups, halogen atoms, cyano groups, lower alkoxy groups, nitro groups, phenyl groups and acyl groups, the process comprising reacting a compound represented by formula (19),

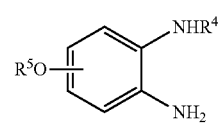
(19)

wherein $R^4$ and $R^5$ are as defined above,
or a salt thereof, and a compound represented by formula (14),

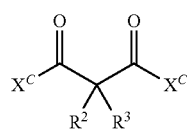
(14)

wherein $R^2$ and $R^3$ are as defined above, and $X^c$, which may be the same or different, represents a halogen atom.

5. The process according to claim 2, wherein the amount of the catalytic hydrogenation reducing agent is 0.1 to 40 wt %, relative to the compound represented by formula (2A).

* * * * *